United States Patent [19]

Dumas

[11] Patent Number: 4,662,932

[45] Date of Patent: May 5, 1987

[54] HERBICIDAL SULFONAMIDES

[75] Inventor: Donald J. Dumas, Wilmington, Del.

[73] Assignee: E. I. Du Pont de Nemours and Company, Wilmington, Del.

[21] Appl. No.: 802,269

[22] Filed: Nov. 27, 1985

Related U.S. Application Data

[63] Continuation-in-part of Ser. No. 705,913, Feb. 26, 1985, abandoned.

[51] Int. Cl.[4] .................... A01N 47/36; C07D 239/42
[52] U.S. Cl. ........................................... 71/92; 71/93; 548/265; 548/268; 544/253; 544/278; 544/321; 544/331; 544/332; 544/208; 544/211
[58] Field of Search ................. 71/92; 544/321, 331, 544/332, 253, 778; 548/265, 268

[56] References Cited

U.S. PATENT DOCUMENTS

| | | | |
|---|---|---|---|
| 4,310,346 | 1/1982 | Levitt | 71/92 |
| 4,339,267 | 7/1982 | Levitt | 71/92 |
| 4,478,635 | 10/1984 | Meyer et al. | 71/92 |
| 4,487,626 | 12/1984 | Zimmerman | 71/90 |
| 4,496,392 | 1/1985 | Levitt | 71/93 |

FOREIGN PATENT DOCUMENTS 0135332  3/1985  European Pat. Off. ............... 71/92

*Primary Examiner*—Robert Gerstl
*Attorney, Agent, or Firm*—James A. Costello

[57] ABSTRACT

Ortho-Hydrazinosulfonyl benzenesulfonylureas, such as 2-(2,2-dimethylhydrazinosulfonyl)-N-[(4,6-dimethoxypyrimidin-2-yl)aminocarbonyl]benzenesulfonamide, are useful as pre-emergent and post-emergent herbicides.

15 Claims, No Drawings

HERBICIDAL SULFONAMIDES

CROSS-REFERENCE TO RELATED APPLICATION

This application is a continuation-in-part of copending application bearing U.S. Ser. No. 705,913, filed on Feb. 26, 1985, now abandoned.

BACKGROUND OF THE INVENTION

Certain ortho-aminosulfonyl benzenesulfonylureas are known as herbicides. U.S. Pat. No. 4,310,346 discloses, in part, herbicidal sulfonamides of formula

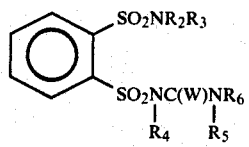

wherein:

$R_2$ is H, $C_1$–$C_6$ alkyl, $C_3$–$C_4$ alkenyl, $C_3$–$C_6$ cycloalkyl, $C_4$–$C_7$ cycloalkylalkyl, $C_5$–$C_6$ cycloalkenyl, $C_3$–$C_5$ alkynyl, $C_3$–$C_6$ cycloalkyl substituted with 1–2 $CH_3$ groups, $CF_2CF_2H$, $CF_2CHFCl$, $CF_2CHFBr$, $CF_2CHFCF_3$, $C(CH_3)_2CN$, $(CH_2)_mCN$, where m is 1 or 2, $CH_2CH_2OCH_3$, $CH_2CH(CH_3)OCH_3$, $(CH_2)_3OCH_3$, $CHR_7CO_2R_8$ or $CHR_7CON(R_8)_2$; and $R_3$ is $C_1$–$C_4$ alkyl, $C_3$–$C_4$ alkenyl, $CH_2CH_2OCH_3$, $CH_2CH(CH)_3OCH_3$, $CH_2CF_3$ or $(CH_2)_mCN$, where m is 1 or 2 or $CHR_7CO_2R_8$.

U.S. Pat. No. 4,478,635 discloses, in part, herbicidal sulfonamides of formula

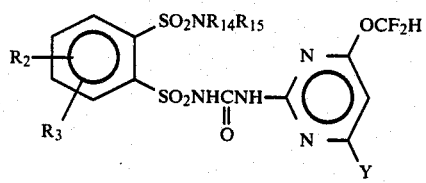

wherein:

$R_{14}$ is H, $OCH_3$, $OC_2H_5$, $C_1$–$C_4$ alkyl or $CO_2R_{12}$; and
$R_{15}$ is H or $C_1$–$C_4$ alkyl.

EPA No. 84305305.9 discloses, in part, herbicidal sulfonylureas of formula

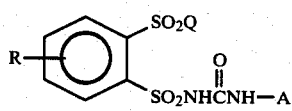

wherein:

Q is $NR_1R_2$,

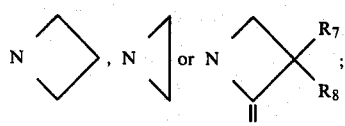

$R_1$ is H, $C(O)R_3$, $C(O)NR_4R_5$, $CO_2R_6$, $C(O)NHR_9$ or $CF_2H$; and $R_2$ is H or $C_1$–$C_3$ alkyl.

U.S. Pat. No. 4,339,267 discloses, in part, herbicidal sulfonamides of formula

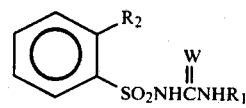

wherein:

$R_1$ is

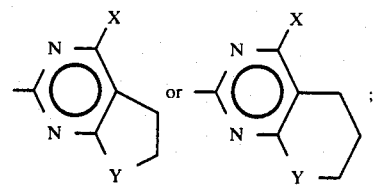

$R_2$ is, among others, $SO_2NR_{10}R_{11}$ or $SO_2N(OCH_3)CH_3$; and $R_{10}$ and $R_{11}$ are independently $C_1$–$C_6$ alkyl or $C_3$–$C_4$ alkenyl or $R_{10}$ and $R_{11}$ can be taken together to be $(CH_2)_4$, $(CH_2)_5$ or $O(CH_2CH_2)_2$.

U.S. Pat. No. 4,487,626 discloses, in part, herbicidal sulfonamides of formula

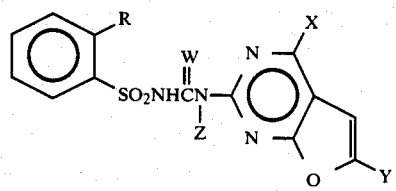

wherein:

R is, among others, $SO_2NR^6R^7$ or $SO_2N(OCH_3)CH_3$; and $R^6$ and $R^7$ are independently $C_1$–$C_4$ alkyl, provided that the total number of carbon atoms of $R^6$ and $R^7$ is less than or equal to 5.

U.S. Pat. No. 4,496,392 discloses, in part, herbicidal sulfonamides of formula

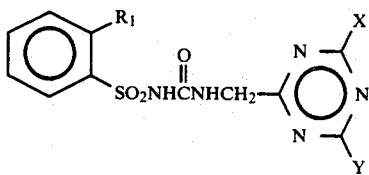

wherein:

$R_1$ is, among others, $SO_2NR_8R_9$ or $SO_2N(CH_3)OCH_3$;
$R_8$ is $CH_3$; and
$R_9$ $C_1$–$C_3$ alkyl.

SUMMARY OF THE INVENTION

The present invention pertains to compounds of Formula I, agriculturally suitable compositions containing selective preemergent and/or postemergent herbicides or plant growth regulants. The compounds of this invention are:

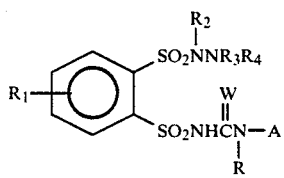

and their agriculturally suitable salts, wherein:

W is O or S;

R is H or $CH_3$;

$R_1$ is H, $C_1$ to $C_3$ alkyl, $C_1$ to $C_3$ haloalkyl, halogen, nitro, $C_1$ to $C_3$ alkoxy, $SO_2NR_aR_b$, $C_1$ to $C_3$ alkylthio, $C_1$ to $C_3$ alkylsulfinyl, $C_1$ to $C_3$ alkylsulfonyl, CN, $CO_2R_c$, $C_1$ to $C_3$ haloalkoxy, $C_1$ to $C_3$ haloalkylthio, $C_2$ to $C_3$ alkoxyalkyl, $C_2$ to $C_3$ haloalkoxyalkyl, $C_2$ to $C_3$ alkylthioalkyl, $C_2$ to $C_3$ haloalkylthioalkyl, $C_2$ to $C_3$ cyanoalkyl or $NR_dR_e$;

$R_a$ is H, $C_1$ to $C_4$ alkyl, $C_2$ to $C_3$ cyanoalkyl, methoxy or ethoxy;

$R_b$ is H, $C_1$ to $C_4$ alkyl or $C_3$ to $C_4$ alkenyl; or $R_a$ and $R_b$ can be taken together as $-(CH_2)_3-$, $-(CH_2)_4-$, $-(CH_2)_5-$ or $-CH_2CH_2OCH_2CH_2-$;

$R_c$ is $C_1$ to $C_4$ alkyl, $C_3$ to $C_4$ alkenyl, $C_3$ to $C_4$ alkynyl, $C_2$ to $C_4$ haloalkyl, $C_2$ to $C_3$ cyanoalkyl, $C_5$ to $C_6$ cycloalkyl, $C_4$ to $C_7$ cycloalkylalkyl or $C_2$ to $C_4$ alkoxyalkyl;

$R_d$ $R_e$ are independently H or $C_1$ to $C_2$ alkyl; $R_2$, $R_3$ and $R_4$ are independently H, $C_1$ to $C_4$ alkyl, $C_3$ to $C_4$ alkenyl, $C_3$ to $C_4$ alkynyl, $C_1$ to $C_4$ haloalkyl, $C(O)R_5$, $CO_2R_6$, $C(O)NR_7R_8$, $C(S)NR_7R_8$, $C(NR)NR_7R_8$, Q, CHRQ, $CH_2CH_2Q$, $C_2$ to $C_3$ alkyl substituted with $OR_9$, phenyl which may be optionally substituted with $R_{10}$ and $R_{11}$ or

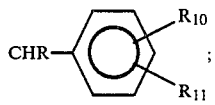

$R_3$ and $R_4$ can be taken together to form $-(CH_2)_4-$, $-(CH_2)_5-$, $CH_2CH_2OCH_2CH_2$, $CH=CHCH=CH$, $CH=N-N=CH$ or

$R_5$ is $C_1$ to $C_3$ alkyl or phenyl which can be optionally substituted with $R_{10}$ and $R_{11}$;

$R_6$ is $C_1$ to $C_3$ alkyl;

$R_7$ and $R_8$ are independently H or $C_1$ to $C_3$ alkyl;

$R_9$ is H, $SO_2R_6$, $C(O)R_6$, $CO_2R_6$, $C(O)NR_7R_8$, $C_1$ to $C_3$ alkyl, $C_1$ to $C_3$ haloalkyl or $P(O)(OR_6)_2$;

$R_{10}$ and $R_{11}$ are independently H, $C_1$ to $C_3$ alkyl, Cl, F, Br, $NO_2$, $CF_3$, CN or $C_1$ to $C_3$ alkoxy;

$R_{12}$ and $R_{13}$ are independently H, $C_1$ to $C_3$ alkyl, phenyl which can be optionally substituted with $R_{10}$ and $R_{11}$ or

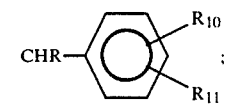

$R_{12}$ and $R_{13}$ can be taken together to form $-(CH_2)_4-$ or $-(CH_2)_5-$;

Q is a saturated 5- or 6-membered ring which is bonded through a carbon atom and contains 1 heteroatom selected from oxygen, sulfur, or nitrogen or an unsaturated or partially unsaturated 5- or 6-membered ring which is bonded through a carbon atom and contains 1 to 3 heteroatoms selected from 1 sulfur, 1 oxygen or 1 to 3 nitrogen; and Q may be optionally substituted by one or more groups selected from L;

L is $C_1$ to $C_4$ alkyl, $C_1$ to $C_3$ haloalkyl, halogen, $C_1$ to $C_3$ alkoxy, $C_1$ to $C_3$ alkylthio, $C_3$ to $C_4$ alkenyloxy, $C_3$ to $C_4$ alkenylthio, $C_1$ to $C_2$ haloalkoxy or $C_1$ to $C_2$ haloalkylthio;

A is

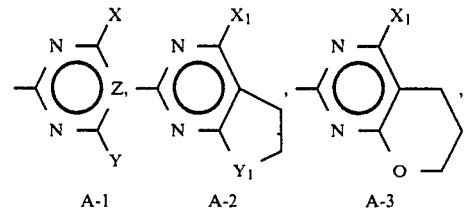

A-1    A-2    A-3

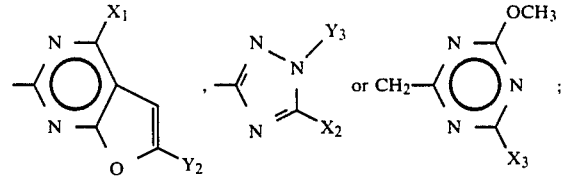

A-4    A-5    A-6

X is H, $C_1$ to $C_4$ alkyl, $C_1$ to $C_4$ alkoxy, $C_1$ to $C_4$ haloalkoxy, $C_1$ to $C_4$ haloalkyl, $C_1$ to $C_4$ haloalkylthio, $C_1$ to $C_4$ alkylthio, halogen, $C_2$ to $C_5$ alkoxyalkyl, $C_2$ to $C_5$ alkoxyalkoxy, amino, $C_1$ to $C_3$ alkylamino or di($C_1$ to $C_3$ alkyl)amino;

Y is H, $C_1$ to $C_4$ alkyl, $C_1$ to $C_4$ alkoxy, $C_1$ to $C_4$ haloalkoxy, $C_1$ to $C_4$ haloalkylthio, $C_1$ to $C_4$ alkylthio, $C_2$ to $C_5$ alkoxyalkyl, $C_2$ to $C_5$ alkoxyalkoxy, amino, $C_1$ to $C_3$ alkylamino, di($C_1$ to $C_3$ alkyl)amino, $C_3$ to $C_4$ alkenyloxy, $C_3$ to $C_4$ alkynyloxy, $C_2$ to $C_5$ alkylthioalkyl, $C_1$ to $C_4$ haloalkyl, $C_3$ to $C_5$ cycloalkyl, $C_2$ to $C_4$ alkynyl, $C(O)R_4$,

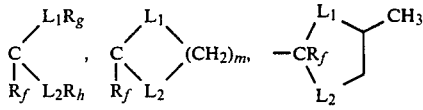

or $N(OCH_3)CH_3$;

m is 2 or 3;

$L_1$ and $L_2$ are independently O or S;

$R_f$ is H or $CH_3$;

$R_g$ and $R_h$ are independently $C_1$ to $C_2$ alkyl;

Z is CH or N;

$Y_1$ is O or $CH_2$;

$X_1$ is $CH_3$, $OCH_3$, $OC_2H_5$ or $OCF_2H$;
$Y_2$ H or $CH_3$;
$X_2$ is $CH_3$, $OCH_3$ or $SCH_3$;
$Y_3$ is $CH_3$, $CH_2CH_3$ or $CH_2CF_3$; and
$X_3$ is $CH_3$ or $OCH_3$;
provided that:
  (a) when X is Cl, F, Br or I, then Z is CH and Y is $OCH_3$, $OC_2H_5$, $N(OCH_3)CH_3$, $NHCH_3$ or $N(CH_3)_2$;
  (b) when X or Y is $OCF_2H$, then Z is CH; and
  (c) the total number of carbon atoms in $R_2$, $R_3$ and $R_4$ does not exceed 10.

In the above definitions, the term "alkyl", used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight-chain or branched alkynes, e.g., ethynyl, 1-propynyl, 2-propynyl and the different butynyl isomers.

Cycloalkyl denotes cyclopropyl, cyclobutyl, cyclopentyl and cyclohexyl.

$C_4$ to $C_7$ cycloalkylalkyl means cyclopropylmethyl through cyclopropylbutyl or cyclohexylmethyl.

The term "halogen", either alone or in compound words such as "haloalkyl", denotes fluorine, chlorine, bromine or iodine. Further, when used in compound words such as "haloalkyl" said alkyl may be monohalogenated or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated by the $C_i$ to $C_j$ prefix where i and j are numbers from 1 to 7. For example, $C_1$ to $C_3$ alkylsulfonyl would designate methylsulfonyl through propylsulfonyl, $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2CH_3$; as a further example, $C_2$ cyanoalkyl would designate $CH_2CN$ and $C_3$ cyanoalkyl would designate $CH_2CH_2CN$ and $CH(CN)CH_3$.

Preferred compounds for reasons of increased ease of synthesis and/or greater herbicidal efficacy are compounds of Formula I wherein:
W is O;
R is H;
$R_1$ is H, $C_1$ to $C_2$ alkyl, F, Cl, Br, $NO_2$, $C_1$ to $C_2$ alkoxy, $C_1$ to $C_2$ alkylthio, $C_1$ to $C_2$ haloalkoxy, $CH_2OCH_3$, $CH_2SCH_3$ or $CH_2CN$ and is not para to the sulfonylurea bridge;
A is A-1;
X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$;
Y is H, $C_1$ to $C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $OCF_2H$, $SCF_2H$, cyclopropyl, $C\equiv CH$, $C\equiv CCH_3$ or $CH(OCH_3)_2$.

More preferred compounds are the "preferred compounds" wherein $R_2$, $R_3$ and $R_4$ are independently H, $C_1$ to $C_3$ alkyl or phenyl provided that one of $R_2$, $R_3$ and $R_4$ must be H.

Most preferred compounds are the "more preferred compounds" wherein $R_1$ is H, Cl, $OCH_3$, $OCF_2H$, $CH_2OCH_3$ or $CH_2CN$; X is $CH_3$, $OCH_3$, $OCH_2CH_3$, Cl, $OCF_2H$ or $OCH_2CF_3$; and Y is $CH_3$, $OCH_3$, $CH_2CH_3$, $CH_2OCH_3$, $NHCH_3$ or $CH(OCH_3)_2$.

Specifically preferred compounds for reasons of greatest ease of synthesis and/or greatest herbicidal efficacy are:
2-(2,2-dimethylhydrazinosulfonyl)-N-[(4,6-dimethoxypyrimidin-2-yl)aminocarbonyl]benzenesulfonamide, m.p. 127° to 128° C.(d); and
2-(2,2-dimethylhydrazinsulfonyl)-N-[(4-methoxy-6-methyl-1,3,5-triazin-2-yl)aminocarbonyl]benzenesulfonamide, m.p. 123° to 124° C.(d).

DETAILED DESCRIPTION OF THE INVENTION

Synthesis

Compounds of Formula I can be prepared by one or more of the procedures shown in Equations 1, 4, and 5. R, $R_1$, $R_2$, $R_3$, $R_4$, and A are as previously defined.

Equation 1

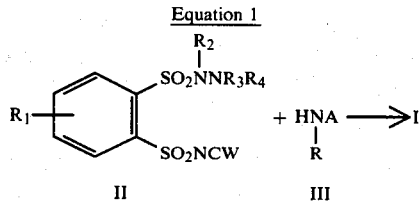

The reaction of Equation 1 is best carried out in an inert aprotic organic solvent such as dichloromethane, 1,2-dichloroethane, tetrahydrofuran, or acetonitrile, at a temperature between 20° and 85° C. The order of addition is not critical; however, it is often convenient to add the sulfonyl isocyanate, or a solution of it in the reaction solvent, to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Sulfonyl isocyanates (II, W is O) are known in the art and are prepared from the corresponding sulfonamides (IV) by one of the following two general methods.

Equation 2

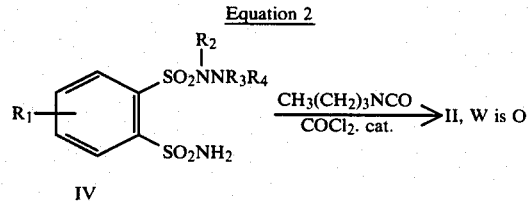

The sulfonamides (IV) is reacted with an alkyl isocyanate (e.g., n-butyl isocyanate) in a solvent whose boiling point is above 135° C., such as xylene. The reaction can optimally be carried out in the presence of a catalytic amount of 1,4-diaza[2.2.2] bicyclooctane (DABCO). The reaction mixture is heated to 135°-140° C. and held at that temperature for 5-60 minutes, after which phosgene is slowly added at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl as isocyanate (II).

If desired, the alkyl isocyanate-sulfonamide adduct can be made and isolated before reaction with the phosgene. In this case the sulfonamide (IV), alkyl isocyanate, and anhydrous base (e.g., $K_2CO_3$) in a polar, aprotic aolvent (e.g. acetone, butanone, or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful when the sulfonamide (IV) is high melting and has low solubility in the phosgenation solvent.

Sulfonyl isocyanate (II, W is O) can also be prepared by the following method.

Equation 3

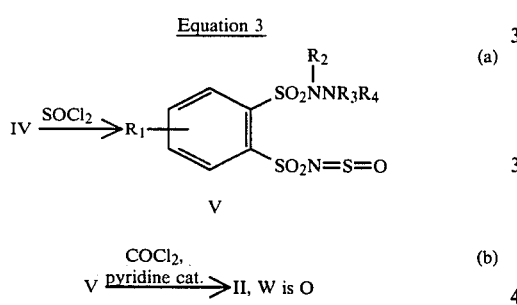

The sulfonamide (IV) is heated at reflux in an excess of thionly chloride. The reaction is continued until the sulfonamide protons are no longer detectable in the proton magnetic resonance spectrum. From 16 hours to 5 days is typically sufficient for complete conversion to the thionylamide (V) (Equation 3a).

The thionyl chloride is evaporated and the residue is treated with an inert solvent (e.g. toluene) containing at least one equivalent (typically 2-3 equivalents) of phosgene. A catalytic amount of pyridine (typically 0.1 equivalent) is added, and the mixture is heated to about 60°-140° C., with 80°-100° preferred. Conversion to the isocyanate (II, W is O) is usually substantially complete within 15 minutes to 3 hours (Equation 3b). The mixture is then cooled and filtered, and the solvent is evaporated, leaving the sulfonyl isocyanate (II, W is O).

Sulfonyl isothiocyanates (II, W is S) are known in the art and are prepared from the corresponding sulfonamides (IV) by reaction with carbon disulfide and potassium hydroxide followed by treatment of the resulting dipotassium salt with phosgene. Such a procedure is described in *Arch. Pharm.* 299, 174 (1966).

Many of the compounds of Formula I can be prepared by the procedure shown in Equation 4.

Equation 4

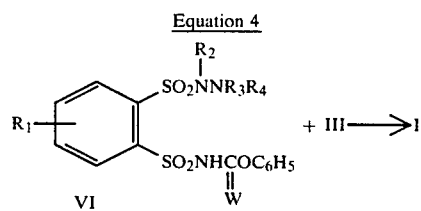

The reaction of Equation 4 is carried out by contacting phenylcarbamates or phenylthiocarbamates of Formula VI with aminoheterocycles of Formula III in an inert organic solvent such as dioxane or tetrahydrofuran at temperatures of about 20°-100° C. for a period of about one-half to twenty-four hours. The product can be isolated by evaporation of the reaction solvent and purified by methods previously described.

Phenylcarbamates and phenylthiocarbamates of Formula VI can be prepared by the methods described, or modifications thereof known to those skilled in the art. One such method is taught in U.S. Pat. No. 4,443,243.

Alternatively, many of the compounds of Formula I can be prepared by the method described in Equation 5.

Equation 5

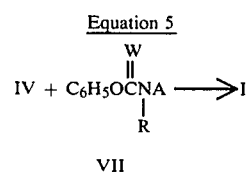

The reaction of Equation 5 can be carried out by contacting equimolar amounts of a sulfonamide of Formula IV with a heterocyclic phenylcarbamate or phenylthiocarbamate of Formula VII in the presence of a base such as 1,8-diazabicyclo[5.4.0]undec-7-ene (DBU), by methods analogous to those described in South African Patent Application No. 83/0441. The phenylcarbamates and phenylthiocarbamates of Formula VII can be prepared by methods, or modifications thereof known to those skilled in the art, described in South African Patent Application No. 82/5671 and South African Patent Application No. 82/5045.

Sulfonamides of formula IV can be prepared by one or both of the procedures shown in Equations 6a and 6b. Equation 6a illustrates the reaction of sulfonyl chlorides of Formula VIII with the appropriate hydrazine derivative of Formula IX to give sulfonyl hydrazides of Formula IV. Equation 6b illustrates the reaction of sulfonyl chlorides of Formula X with ammonia to give compounds of Formula IV wherein $R_1$, $R_2$, $R_3$, and $R_4$ are as previously defined.

Equation 6

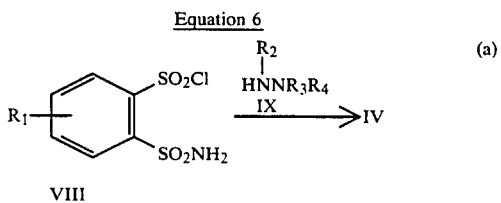

-continued
Equation 6

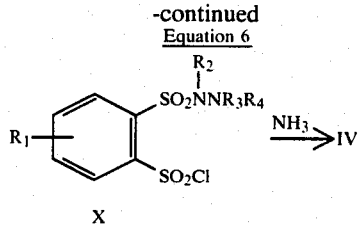

(b)

The reactions of Equations 6a and 6b are preferably carried out in an inert, aprotic solvent such as methylene chloride, tetrahydrofuran, or acetonitrile at a temperature between −78° and 40° C. These reactions require the presence of a scavenger for the by-product hydrochloric acid. This can be accomplished by the use of a two-fold excess of ammonia or the hydrazine derivative or by the addition of an equivalent of a base such as triethylamine, pyridine, or aqueous sodium hydroxide. In cases in which the products are insoluble in the reaction solvent, they may be isolated by simple filtration followed by washing with water to remove hydrochloride salts. When the products are soluble, they can be isolated by filtration, to remove any insoluble salts, followed by evaporation of the solvent and trituration of the residue with solvents such as 1-chlorobutane, diethyl ether or ethyl acetate, and filtration. In some cases it is helpful to wash the product with water to remove residual salts.

Sulfonyl chlorides of Formula VIII where $R_1$ is as previously defined can be prepared by the methods shown in Equations 7 and 8.

Diazotization of appropriately substituted aniline derivatives of Formula XI as shown in Equation 7, and subsequent coupling with sulfur dioxide in the presence of either cupric or cuprous chloride gives the desired products of Formula VIII. This reaction can be accomplished by methods described, or modifications thereof known to those skilled in the art, in the Journal of Pharmacy and Pharmacology, Vol. 12, pages 648 to 655 (1960).

Equation 7

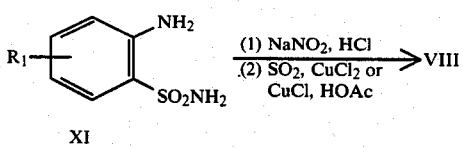

The reaction of Equation 7 can be affected by analogous methods described in U.S. Pat. No. 4,310,346. In Equation 7, a substituted aniline XI, wherein $R_1$ is not $NR_dR_e$ in concentrated hydrochloric acid is treated with a solution of sodium nitrite in water at −5° to 5° C. After being stirred for 10–30 minutes at about 0° C., the solution is added to a mixture of excess sulfur dioxide and a catalytic amount of cupric or cuprous chloride in acetic acid at about 10° C. After stirring for 0.25 to 24 hours at temperatures between 10° to 25° C., the solution is poured into a large excess of ice water. The sulfonyl chlorides VIII can be isolated by filtration, or by extraction into a solvent such as methylene chloride or diethyl ether, followed by drying and evaporation of the solvent.

Oxidative chlorination of appropriately substituted arylthioethers of Formula XII give the desired products wherein $R_{13}$ is $C_2$ to $C_4$ alkyl or benzyl and $R_1$ is not $C_1$ to $C_3$ alkylthio, $C_1$ to $C_3$ alkylsulfinyl, $C_1$ to $C_3$ haloalkylthio, $C_2$ to $C_3$ alkylthioalkyl or $C_2$ to $C_3$ haloalkylthioalkyl.

Equation 8

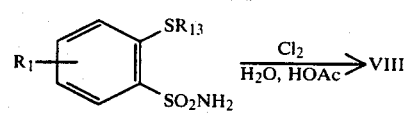

The reaction of Equation 8 can be carried out by treating a solution of the thioether XII in a solvent such as acetic acid in the presence of at least 2.5 equivalents of water and at least 3.0 equivalents of chlorine at 0°–30° C. for 0.25 to 5 hours. The reaction is poured into ice-water and the product is isolated by extraction with a suitable solvent such as methylene chloride, dried, and the solvent evaporated to yield a product sufficiently pure to be carried directly on to the next step.

Sulfonyl chlorides of Formula X in Equation 6b can be prepared by the procedure shown in Equation 9 wherein $R_1$, $R_2$, $R_3$, and $R_4$ are as previously defined. This procedure is best suited to cases in which both $R_3$ and $R_4$ are other than H.

Diazotization of appropriately substituted aniline derivatives of Formula XIII, as shown in Equation 9, and subsequent coupling with sulfur dioxide in the presence of either cupric or cuprous chloride give the desired products of Formula X.

Equation 9

R₁—[benzene ring]—SO₂NNR₃R₄ (R₂), NH₂ →(1) NaNO₂ (2) SO₂, CuCl₂ or CuCl, HOAc→ X

XIII

The reactions of Equation 9, wherein $R_1$ is not $NR_dR_e$, can be carried out under the conditions described for the reactions of Equation 7.

Aniline derivatives of Formula XI in Equation 7 can be prepared as shown in Equation 10 by reduction of the corresponding nitro compounds of Formula XIV wherein $R_1$ is other than $NO_2$.

Equation 10

R₁—[benzene ring]—NO₂, SO₂NH₂ →[H]→ XI

XIV

The reduction reactions of Equation 10 can be accomplished by methods known in the literature by those skilled in the art. For details see, for example, U.S. Pat. No. 4,511,392 and references cited therein.

The nitro compounds of Formula XIV are well known in the art and can be prepared by methods such as those described in U.S. Pat. No. 4,120,691.

The arylthioethers of Formula XII in Equation 8 are known in the art and can be prepared by methods described in U.S. Pat. No. 4,371,391.

The aniline derivatives of Formula XIII in Equation 9 can be prepared as shown in Equation 11 by reduction of the corresponding nitro compounds of Formula XV wherein $R_1$ is other than $NO_2$.

Equation 11

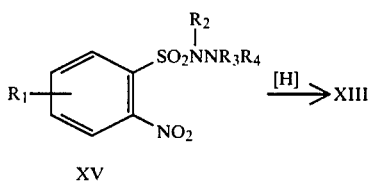

The reaction of Equation 11 can be carried out under the conditions described for Equation 10.

Compounds of Formula XV can be prepared as shown in Equation 12 by the reaction of ortho-nitrobenzenesulfonyl chlorides of Formula XVI with the appropriate hydrazine derivatives of Formula IX to give ortho-nitrobenzenesulfonyl hydrazides of Formula XV.

Equation 12

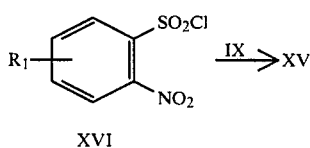

The reaction of Equation 12 can be carried out under the conditions described for Equation 6.

Sulfonyl chlorides of Formula XVI are known in the art and can be prepared by methods described in U.S. Pat. No. 4,120,691.

The hydrazine, benzoyl hydrazine, acyl hydrazine, hydrazinocarboxylate, semmicarbazide, thiosemicarbazide, and aminoquanidine derivatives of Formula IX in Equations 6a ad 12 are known in the art or can be prepared by one skilled in the art using methods such as those reviewed by E. W. Schmidt in *Hydrazine and its Derivatives: Preparation, Properties, Applications*, J. Wiley, New York, 1984 and by Smith in *Derivatives of Hydrazine and Other Hydronitrogens Having N—N Bonds*, Benjamin/Cummings, Reading, Mass., 1983.

The preparation of compounds of Formula I with certain combinations of the substitutents $R_2$, $R_3$, and $R_4$ may be more conveniently achieved using a sulfonylurea of Formula I or a sulfonamide of Formula IV as the intermediate. For example, sulfonylureas of Formula I in which both $R_3$ and $R_4$ are H may be prepared by acid catalyzed hydrolysis of compounds of Formula I in which $R_3$ and $R_4$ are taken together to form $=CR_{12}R_{13}$. This and other transformations may be accomplished by procedures which are known in the literature by those skilled in the art.

In cases where $R_2$, $R_3$, or $R_4$ is $C_1$–$C_6$ alkyl substituted with $OSO_2R_5$, $OC(O)R_5$, $OCO_2R_5$, $OC(O)NR_7R_8$, or $OP(O)(OR_5)_2$ it is often more convenient to first prepare the corresponding sulfonamides of Formula IV or sulfonylureas of Formula I in which $R_2$, $R_3$, or $R_4$ is $C_1$–$C_6$ alkyl substituted with OH. The hydroxy group can then be functionalized to give the desired derivatives using methods which are well know in the art.

The heterocyclic amines of Formula III in Equation 3 above can be prepared by methods known in the literature, or simple modifications thereof, by those skilled in the art. For instance, EP-A No. 84,224 (published July 27, 1983) and W. Braker et al., *J. Chem Soc.*, 69, 3072 (1947) describes methods for preparing aminopyridines and triazines substituted by acetal groups such as dialkoxymethyl or 1,3-dioxolan-2-yl, among other groups. Also, for example, South African patent application Nos. 82/5045 and 82/5671 describe methods for preparing aminopyrimidines and triazines substituted by haloalkyl or haloalkythio groups such as $OCH_2CH_2F$, $OCH_2CF_3$, $SCF_2H$, or $OCF_2H$, among other groups. South African Patent Application No. 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2,3-d]pyrimidine-2-amines, the cyclopenta[d]pyrimidines-2-amines (III, A is A-2) and the 6,7-dihydro-5H-pyrano[2.3-d]pyrimidin-2-amines (III, A is A-3) are described in U.S. Pat. No. 4,487,626.

Compounds of Formula III, where A is A-5, are described in U.S. Pat. No. 4,421,550. Compounds of Formula III, where A is A-6, are described in U.S. Pat. No. 4,496,392.

In addition, general methods for preparing aminopyrimidines and triazines have been reviewed in the following publications:

"The Chemistry of Heterocyclic Compounds", a series published by Interscience Publishers, Inc., New York and London;

"Pyrimidines", Vol. 16 of the same series by D. J. Brown;

"s-Triazines and Derivatives": Vol. 12 of the same series by E. M. Smolin and L. Rappoport; and F. C. Schaefer, U.S. Pat. No. 3,154,547 and K. R. Huffman and F. C., Schaefer, *J. Org. Chem.*, 28, 1812 (1963), which describes the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

2-(2,2-Dimethylhydrazinosulfonyl)-benzenesulfonamide

A solution of 1.28 g of 2-(aminosulfonyl)benzenesulfonyl chloride in 12 mL of dry tetrahydrofuran (THF) was cooled to $-65°$ C. and a solution of 0.88 mL of 1,1-dimethylhydrazine in 12 mL of dry THF added dropwise. The resulting mixture was allowed to warm to room temperature, filtered, and the filtrate concentrated in vacuo. The solid residue was partitioned between water and ethyl acetate, the organic phase was separated, washed with water, washed with brine, dried ($MgSO_4$), concentrated in vacuo, and the residue triturated with 1-chlorobutane to provide 1.07 g of the subject compound, m.p. 122°–124° C. (dec).

NMR ($CDCl_3$/DMSO-$d_6$)$\delta$: 2.37 (s, 6H, N($CH_3$)$_2$), 6.9 (br s, 2H, $SO_2NH_2$), 7.1 (br s, 1H, $SO_2N\underline{H}NMe_2$), 7.75–7.9 (m, 2H, aromatics), 8.25–8.4 (m, 2H, aromatics).

EXAMPLE 2

2-(2,2-Dimethylhydrazinosulfonyl)-N-[(4,6-dimethoxypyrimidin-2-yl)aminocarbonyl]benzenesulfonamide To a solution of 0.14 g of the product of Example 1 and 0.15 g of phenyl(4,6-dimethoxypyrimidin-2-yl)carbamate in 2 mL of dry acetonitrile was added 0.1 mL of 1,5-diazabicyclo[5.4.0]undec-5-ene. The solution was stirred for 15 minutes at room temperature, diluted with 2 mL of water and acidified with 5% hydrochloric acid to a pH of 4. The precipitated product was collected by filtration, washed thoroughly with water, washed with 1-chlorbutane, and dried in vacuo at 40° C. to afford 0.02 g of the subject compound, m.p. 127°–128° C. (dec).

NMR($CDCl_3$)$\delta$: 2.37 (s, 6H, N($CH_3$)$_2$), 3.99 (s, 6H, $OCH_3$'s), 5.77 (s, 1H, pyr. C5-H), 6.72 (br s, 1H, $SO_2NH$ $NMe_2$), 7.18 (br s, 1H, C($=$O)N$\underline{H}$ pyr.), 7.82 (m, 2$\overline{H}$, aromatics), 8.31 (m, 1H, aromati$\overline{c}$), 8.56 (m, 1H, aromatic), 12.68 (br s, 1H, $SO_2NHCO$).

IR (nujol) 1730, 1710 $cm^{-1}$ (C$=$O).

Using the methods described in Equations 1 to 12 and Examples 1 and 2, or simple modifications thereof, the compounds of Tables I, Ia, II and IIa can be prepared.

TABLE I

Formula I, A = A-1, W = O

| R | $R_1$ | $R_2$ | $R_3$ | $R_4$ | X | Y | Z | m.p. (°C.) |
|---|---|---|---|---|---|---|---|---|
| H | H | H | H | H | $CH_3$ | $CH_3$ | CH | |
| H | H | H | H | H | $OCH_3$ | $OCH_3$ | CH | |
| H | H | H | H | H | $OCH_3$ | $CH_3$ | N | |
| H | H | H | H | $CH_3$ | $OCH_3$ | $OCH_3$ | N | |
| H | H | H | H | $CH_3$ | $OCH_3$ | $OCH_3$ | CH | |
| H | H | H | H | $CH_3$ | $OCH_3$ | $OCH_3$ | CH | |
| H | H | H | H | $CH_3$ | Cl | $OCH_3$ | CH | |
| H | H | H | H | $CH_3$ | $CH_3$ | $CH_3$ | CH | |
| H | H | H | H | $C_2H_5$ | $CH_3$ | $CH_3$ | CH | |
| H | H | H | H | $C_2H_5$ | $OCH_3$ | $OCH_3$ | N | |
| H | H | H | H | $C_2H_5$ | $CH_3$ | $OCH_3$ | N | |
| H | H | H | H | iso-$C_3H_7$ | $CH_3$ | $CH_3$ | CH | |
| H | H | H | H | iso-$C_3H_7$ | $OCH_3$ | $OCH_3$ | CH | |
| H | H | H | H | n-$C_4H_7$ | $CH_3$ | $CH_3$ | CH | |
| H | H | H | H | n-$C_4H_7$ | $OCH_3$ | $OCH_3$ | CH | |
| H | H | H | H | $CH_2CH=CH_2$ | $OCH_3$ | $OCH_3$ | N | |
| H | H | H | H | $CH_2CH=CH_2$ | $OCH_3$ | $OCH_3$ | CH | |
| H | H | H | H | $CH_2C≡CCH_3$ | $CH_3$ | $CH_3$ | CH | |
| H | H | H | H | $CH_2C≡CCH_3$ | $OCH_3$ | $OCH_3$ | CH | |
| H | H | H | H | $CH_2CF_3$ | $CH_3$ | $CH_3$ | CH | |
| H | H | H | H | $CH_2CF_3$ | $OCH_3$ | $OCH_3$ | N | |
| H | H | H | H | $CH_2CH_2CH_2CH_2Cl$ | $OCH_3$ | $OCH_3$ | N | |
| H | H | H | H | $CH_2CH_2CH_2CH_2Cl$ | $OCH_3$ | $CH_3$ | N | |
| H | H | H | $C_6H_5$ | H | $OCH_3$ | $CH_3$ | CH | |
| H | H | H | $C_6H_5$ | H | Cl | $CH_3$ | CH | |
| H | H | H | $C_6H_5$ | H | $CH_3$ | $CH_3$ | CH | |
| H | H | H | $C_6H_5$ | H | $N(CH_3)_2$ | $C≡CH$ | CH | |
| H | H | H | $C_6H_5$ | H | $CH_3$ | $OCH_3$ | CH | |
| H | H | H | 2-F—$C_6H_5$ | H | $OCH_3$ | $OCH_3$ | CH | |
| H | H | H | 2-F—$C_6H_4$ | H | $OCH_3$ | $OCH_3$ | CH | |
| H | H | H | 3-F—$C_6H_4$ | H | $OCH_3$ | $OCH_3$ | CH | |
| H | H | H | 4-F$C_6H_4$ | H | $OCH_3$ | $OCH_3$ | CH | |
| H | H | H | 2-Cl$C_6H_4$ | H | $OCH_3$ | $OCH_3$ | CH | |
| H | H | H | 4-Cl$C_6H_4$ | H | $OCH_3$ | $OCH_3$ | CH | |
| H | H | H | 4-Br$C_6H_4$ | H | $OCH_3$ | $OCH_3$ | CH | |
| H | H | H | 2-$CH_3C_6H_4$ | H | $OCH_3$ | $OCH_3$ | CH | |
| H | H | H | 3-$NO_2C_6H_4$ | H | $OCH_3$ | $OCH_3$ | CH | |
| H | H | H | 4-$CF_3C_6H_4$ | H | $OCH_3$ | $OCH_3$ | CH | |
| H | H | H | 4-$CNC_6H_4$ | H | $OCH_3$ | $OCH_3$ | CH | |
| H | H | H | 3-$CH_3OC_6H_4$ | H | $OCH_3$ | $OCH_3$ | CH | |
| H | H | H | 4-$C_2H_5OC_6H_4$ | H | $OCH_3$ | $OCH_3$ | CH | |
| H | H | H | 4-Cl-2-$CH_3C_6H_3$ | H | $OCH_3$ | $OCH_3$ | CH | |
| H | H | H | 2,4-diCl$C_6H_3$ | H | $OCH_3$ | $OCH_3$ | CH | |
| H | H | H | 4-iso$C_3H_7C_6H_4$ | H | $OCH_3$ | $OCH_3$ | CH | |
| H | H | H | 4-pyridyl | H | $OCH_3$ | $OCH_3$ | CH | |
| H | H | H | 4-$CH_3$—6-$CH_3O$ pyrimidin-2-yl | H | $OCH_3$ | $OCH_3$ | CH | |
| H | H | H | 5-$CH_3$—1,3,4-oxadiazol-2-yl | H | $OCH_3$ | $OCH_3$ | CH | |
| H | H | H | 2-thienyl | H | $OCH_3$ | $OCH_3$ | CH | |
| H | H | H | tetrahydro-2-furanyl | H | $OCH_3$ | $OCH_3$ | CH | |

TABLE I-continued

Formula I, A = A-1, W = O

| R | R₁ | R₂ | R₃ | R₄ | X | Y | Z | m.p. (°C.) |
|---|---|---|---|---|---|---|---|---|
| H | H | H | 2-CH₂—thienyl | H | OCH₃ | OCH₃ | CH | |
| H | H | H | 2-CH₂CH₂tetrahydrofuranyl | H | OCH₃ | OCH₃ | CH | |
| H | H | CH₃ | H | H | OCH₃ | OCH₃ | CH | |
| H | H | CH₃ | H | H | OCH₃ | CH₃ | N | |
| H | H | COCH₃ | H | H | OCH₃ | CH₃ | N | |
| H | H | COCH₂CH₃ | H | H | OCH₃ | CH₃ | N | |
| H | H | COC₆H₅ | H | H | OCH₃ | CH₃ | N | |
| H | H | COC₆H₄—4-Cl | H | H | OCH₃ | CH₃ | N | |
| H | H | CO₂C₂H₅ | H | H | OCH₃ | CH₃ | N | |
| H | H | CON(C₂H₅)₂ | H | H | OCH₃ | CH₃ | N | |
| H | H | CSN(CH₃)₂ | H | H | OCH₃ | CH₃ | N | |
| H | H | C₂H₅ | CH₃ | H | OCH₃ | OCH₃ | CH | |
| H | H | C₂H₅ | CH₃ | H | OCH₃ | OCH₃ | CH | |
| H | H | C₂H₄OH | CH₃ | H | OCH₃ | OCH₃ | CH | |
| H | H | C₂H₄OC(O)CH₃ | CH₃ | H | OCH₃ | OCH₃ | CH | |
| H | H | C₂H₄OP(O)(OCH₃)₂ | CH₃ | H | OCH₃ | OCH₃ | CH | |
| H | H | CH₃ | C₆H₅ | H | OCH₃ | OCH₃ | CH | |
| H | H | C₂H₅ | C₆H₅ | H | OCH₃ | OCH₃ | CH | |
| H | H | n-C₄H₉ | C₆H₅ | H | OCH₃ | OCH₃ | CH | |
| H | H | CH₂CH=CH₂ | C₆H₅ | H | OCH₃ | OCH₃ | CH | |
| H | H | CH₂CH₂F | C₆H₅ | H | OCH₃ | OCH₃ | CH | |
| H | H | COCH₃ | C₆H₅ | H | OCH₃ | OCH₃ | CH | |
| H | H | COCH₂CH₃ | C₆H₅ | H | OCH₃ | OCH₃ | CH | |
| H | H | COCH₂CH₂CH₃ | C₆H₅ | H | OCH₃ | OCH₃ | CH | |
| H | H | COC₆H₅ | C₆H₅ | H | OCH₃ | OCH₃ | CH | |
| H | H | COC₆H₄—4-CH₃ | C₆H₅ | H | OCH₃ | OCH₃ | CH | |
| H | H | COC₆H₄—2-Cl | C₆H₅ | H | OCH₃ | OCH₃ | CH | |
| H | H | CO₂C₂H₅ | C₆H₅ | H | OCH₃ | OCH₃ | CH | |
| H | H | CONHCH₂CH₃ | C₆H₅ | H | OCH₃ | OCH₃ | CH | |
| H | H | C(NH)N(CH₃)₂ | C₆H₅ | H | OCH₃ | OCH₃ | CH | |
| H | H | CH₂CH₂OH | C₆H₅ | H | OCH₃ | OCH₃ | CH | |
| H | H | CH₂CH₂OSO₂CH₃ | C₆H₅ | H | OCH₃ | OCH₃ | CH | |
| H | H | CH₂CH₂CH₂OCOCH₃ | C₆H₅ | H | OCH₃ | OCH₃ | CH | |
| H | H | CH₂CH₂OCOC₃H₇ | C₆H₅ | H | OCH₃ | OCH₃ | CH | |
| H | H | CH₂OCON(CH₃)₂ | C₆H₅ | H | OCH₃ | OCH₃ | CH | |
| H | H | CH₃ | CH₃ | H | OCH₃ | OCH₃ | CH | |
| H | H | CH₃ | CH₃ | H | Cl | OCH₃ | CH | |
| H | H | CH₃ | CH₃ | H | CH₃ | CH₃ | CH | |
| H | H | CH₃ | CH₃ | H | CH₃ | OCH₃ | CH | |
| H | H | CH₃ | CH₃ | H | CH₃ | CH₃ | N | |
| H | H | CH₃ | CH₃ | H | OCH₃ | OCH₃ | N | |
| H | H | CH₃ | CH₃ | H | OC₂H₅ | C≡CH | N | |
| H | H | CH₃ | CH₃ | H | CH₃ | C≡CH | N | |
| H | H | CH₃ | CH₃ | H | N(CH₃)₂ | C≡CH | CH | |
| H | H | CH₃ | CH₃ | H | Br | C≡CH | CH | |
| H | H | CH₃ | CH₃ | H | OCH₂F | OCH₃ | CH | |
| H | H | CH₃ | CH₃ | H | OCH₂CF₃ | OCH₃ | CH | |
| H | H | CH₃ | CH₃ | H | CF₃ | CF₃ | CH | |

TABLE I-continued

Formula I, A = A-1, W = O

| R | R₁ | R₂ | R₃ | R₄ | X | Y | Z | m.p. (°C.) |
|---|----|----|----|----|---|---|---|------------|
| H | H | CH₃ | CH₃ | H | CH₃ | N(CH₃)₂ | CH | |
| H | H | CH₃ | CH₃ | H | CH₃ | NH(CH₃)₂ | CH | |
| H | H | CH₃ | CH₃ | H | CH₃ | CH₂OCH₃ | CH | |
| H | H | CH₃ | CH₃ | H | CH₃ | OC₂H₅ | CH | |
| H | H | CH₃ | CH₃ | H | CH₃ | CH₂SCH₃ | CH | |
| H | H | CH₃ | CH₃ | H | CH₂Cl | SCH₃ | CH | |
| H | H | CH₃ | CH₃ | H | CH₂CHF₂ | CH₃ | CH | |
| H | H | CH₃ | CH₃ | H | OCH₃ | CH₃ | CH | |
| H | H | C₆H₅ | C₆H₅ | H | F | OCH₂CH₂OCH₃ | CH | |
| H | H | C₆H₅ | 2-Cl—C₆H₄ | H | Cl | OCH₃ | CH | |
| H | H | C₆H₅ | 4-CH₃O—C₆H₄ | H | Br | OCH₃ | CH | |
| H | H | H | CH₃ | CH₃ | I | OCH₃ | CH | |
| H | H | H | CH₃ | CH₃ | OCH₂F | OCH₃ | CH | 115-116(d) |
| H | H | H | CH₃ | CH₃ | Cl | OCH₃ | CH | |
| H | H | H | CH₃ | CH₃ | OCF₂H | OCH₃ | CH | 127-128(d) |
| H | H | H | CH₃ | CH₃ | OCH₂CH₂F | OCH₃ | CH | 120-122(d) |
| H | H | H | CH₃ | CH₃ | OCH₂CHF₂ | OCH₃ | CH | 125-127(d) |
| H | H | H | CH₃ | CH₃ | OCH₂CF₃ | OCH₃ | CH | |
| H | H | H | CH₃ | CH₃ | OCH₃ | OCH₃ | CH | |
| H | H | H | CH₃ | CH₃ | CH₃ | CH₃ | CH | |
| H | H | H | CH₃ | CH₃ | CH₃ | CF₃ | CH | |
| H | H | H | CH₃ | CH₃ | CH₃ | H | CH | |
| H | H | H | CH₃ | CH₃ | CH₃ | n-C₃H₇ | CH | |
| H | H | H | CH₃ | CH₃ | CH₃ | OC₂H₅ | CH | |
| H | H | H | CH₃ | CH₃ | OCH₃ | CH₂OCH₃ | CH | |
| H | H | H | CH₃ | CH₃ | CH₃ | NHCH₃ | CH | |
| H | H | H | CH₃ | CH₃ | CH₃ | N(OCH₃)CH₃ | CH | |
| H | H | H | CH₃ | CH₃ | CH₃ | N(CH₃)₂ | CH | |
| H | H | H | CH₃ | CH₃ | CH₃ | SCH₃ | CH | |
| H | H | H | CH₃ | CH₃ | CH₃ | OCH₂C=CH | CH | |
| H | H | H | CH₃ | CH₃ | CH₃ | cyclopropyl | CH | |
| H | H | H | CH₃ | CH₃ | CH₃ | C≡CH | N | |
| H | H | H | CH₃ | CH₃ | OCH₃ | C≡CH | N | |
| H | H | H | CH₃ | CH₃ | OCH₃ | CH₃ | N | |
| H | H | H | CH₃ | CH₃ | OC₂H₅ | OCH₃ | N | |
| H | H | H | CH₃ | CH₃ | NHCH₃ | NHCH₃ | N | |
| H | H | H | CH₃ | CH₃ | CF₃ | CF₃ | CH | |
| H | H | H | CH₃ | CH₃ | CF₃ | CH₃ | CH | 123-124(d) |
| H | H | H | CH₃ | CH₃ | CH₃ | C₂H₅ | CH | 132-133(d) |
| H | H | H | CH₃ | CH₃ | CH₃ | n-C₃H₇ | CH | |
| H | H | H | CH₃ | CH₃ | CH₃ | SCH₃ | N | |
| H | H | H | CH₃ | CH₃ | CH₃ | OCH₂CH=CH₂ | CH | |
| H | H | H | CH₃ | CH₃ | CH₃ | OCH₂OCH₂CH₃ | N | |
| H | H | H | CH₃ | CH₃ | CH₃ | OCH₂CH₂OCH₃ | N | |
| H | H | H | CH₃ | CH₃ | CH₃ | CH₂SCH₃ | N | |
| H | H | H | CH₃ | CH₃ | CH₃ | NH₂ | CH | |

TABLE I-continued

Formula I, A = A-1, W = O

| R | R$_1$ | R$_2$ | R$_3$ | R$_4$ | X | Y | Z | m.p. (°C.) |
|---|---|---|---|---|---|---|---|---|
| H | H | H | CH$_3$ | CH$_3$ | CH$_3$ | OCH$_2$CF$_3$ | N | |
| H | H | H | CH$_3$ | CH$_3$ | CH$_3$ | SCH$_2$F | N | |
| H | H | H | CH$_3$ | CH$_3$ | CH$_3$ | OCH$_2$C≡CH | N | |
| H | H | H | CH$_3$ | CH$_3$ | CH$_3$ | COCH$_3$ | CH | |
| H | H | H | CH$_3$ | CH$_3$ | CH$_3$ | CH(OCH$_3$)$_2$ | CH | |
| H | H | H | CH$_3$ | CH$_3$ | CH$_3$ | 1,3-dithiolan-2-yl | CH | |
| H | H | H | CH$_3$ | CH$_3$ | CH$_3$ | 1,3-oxathian-2-yl | CH | |
| H | H | H | CH$_3$ | CH$_3$ | CH$_3$ | 1,3-dioxolan-2-yl | CH | |
| H | H | H | CH$_3$ | CH$_3$ | OCH$_2$F | OCH$_2$F | CH | |
| H | H | H | CH$_3$ | CH$_3$ | CH$_3$ | SCF$_2$H | CH | |
| H | H | H | CH$_3$ | CH$_3$ | CH$_3$ | C≡CCH$_3$ | CH | |
| H | H | H | CH$_3$ | CH$_2$CH$_2$CH$_3$ | CH$_3$ | OCH$_3$ | N | |
| H | H | H | CH$_3$ | CH═CH$_2$ | CH$_3$ | OCH$_3$ | N | |
| H | H | H | CH$_3$ | C$_6$H$_5$ | CH$_3$ | OCH$_3$ | N | |
| H | H | H | —CH$_2$CH$_2$CH$_2$— | | CH$_3$ | OCH$_3$ | N | |
| H | H | H | —CH$_2$CH$_2$CH$_2$CH$_2$— | | CH$_3$ | OCH$_3$ | N | |
| H | H | H | —CH$_2$CH$_2$OCH$_2$CH$_2$— | | CH$_3$ | OCH$_3$ | N | |
| H | H | H | —CH═CH—CH═CH— | | CH$_3$ | OCH$_3$ | N | |
| H | H | H | —CH═NN═CH— | | CH$_3$ | OCH$_3$ | N | |
| H | H | H | ═CHCH$_3$ | | CH$_3$ | OCH$_3$ | N | |
| H | H | H | ═CHC$_6$H$_5$ | | CH$_3$ | OCH$_3$ | N | |
| H | H | H | ═C(CH$_3$)$_2$ | | CH$_3$ | OCH$_3$ | N | |
| H | H | H | ═C(CH$_3$)CH$_2$C$_6$H$_5$ | | CH$_3$ | OCH$_3$ | N | |
| H | H | H | ═C(C$_6$H$_5$)$_2$ | | CH$_3$ | OCH$_3$ | N | |
| H | H | H | ═C(C$_2$H$_5$)C$_6$H$_5$ | | CH$_3$ | OCH$_3$ | N | |
| H | H | H | ═C(C$_2$H$_5$)C$_6$H$_4$-4-CH$_3$O | | CH$_3$ | OCH$_3$ | N | |
| H | H | H | —CH$_2$CH$_2$CH$_2$— | | CH$_3$ | OCH$_3$ | CH | |
| H | H | COCH$_3$ | CH$_3$ | CH$_3$ | CH$_3$ | OCH$_3$ | CH | |
| H | H | COCH$_3$ | CH$_3$ | C$_6$H$_5$ | CH$_3$ | OCH$_3$ | CH | |
| H | H | COCH$_3$ | C$_6$H$_5$ | C$_6$H$_5$ | CH$_3$ | OCH$_3$ | CH | |
| H | H | COCH$_3$ | CH$_3$ | C$_6$H$_4$-3-Cl | CH$_3$ | OCH$_3$ | CH | |
| H | H | CH$_3$ | CH$_3$ | CH$_3$ | CH$_3$ | OCH$_3$ | CH | |
| H | H | C$_2$H$_5$ | CH$_3$ | C$_6$H$_5$ | CH$_3$ | OCH$_3$ | CH | |
| H | H | CH$_3$ | C$_6$H$_5$ | C$_6$H$_5$ | CH$_3$ | OCH$_3$ | CH | |
| H | H | CH$_3$ | CH$_3$ | CH$_3$ | CH$_3$ | OCH$_3$ | CH | |
| H | 3-CH$_3$ | H | CH$_3$ | CH$_3$ | CH$_3$ | OCH$_3$ | CH | |
| H | 4-C$_2$H$_5$ | H | CH$_3$ | CH$_3$ | CH$_3$ | OCH$_3$ | CH | |
| H | 5-iso-C$_3$H$_7$ | H | CH$_3$ | CH$_3$ | CH$_3$ | OCH$_3$ | CH | |
| H | 5-CF$_3$ | H | CH$_3$ | CH$_3$ | CH$_3$ | OCH$_3$ | CH | |
| H | 4-F | H | CH$_3$ | CH$_3$ | CH$_3$ | OCH$_3$ | CH | |
| H | 4-Cl | H | CH$_3$ | CH$_3$ | CH$_3$ | OCH$_3$ | CH | |
| H | 4-Br | H | CH$_3$ | CH$_3$ | CH$_3$ | OCH$_3$ | CH | |
| H | 4-CH$_3$O | H | CH$_3$ | CH$_3$ | CH$_3$ | OCH$_3$ | CH | |
| H | 5-F | H | CH$_3$ | CH$_3$ | OCH$_3$ | OCH$_3$ | CH | |
| H | 5-Cl | H | CH$_3$ | CH$_3$ | OCH$_3$ | OCH$_3$ | CH | |
| H | 5-Br | H | CH$_3$ | CH$_3$ | OCH$_3$ | OCH$_3$ | CH | |
| H | 5-I | H | CH$_3$ | CH$_3$ | OCH$_3$ | OCH$_3$ | CH | |
| H | 5-NO$_2$ | H | CH$_3$ | CH$_3$ | OCH$_3$ | OCH$_3$ | CH | |
| H | 5-CH$_3$O | H | CH$_3$ | CH$_3$ | OCH$_3$ | OCH$_3$ | CH | |
| H | 5-C$_2$H$_5$O | H | CH$_3$ | CH$_3$ | OCH$_3$ | OCH$_3$ | CH | |
| H | 5-C$_3$H$_7$O | H | CH$_3$ | CH$_3$ | OCH$_3$ | OCH$_3$ | CH | |

TABLE I-continued

Formula I, A = A-1, W = O

| R | R₁ | R₂ | R₃ | R₄ | X | Y | Z | m.p. (°C.) |
|---|---|---|---|---|---|---|---|---|
| H | 5-SCH₃ | H | CH₃ | CH₃ | OCH₃ | OCH₃ | CH | |
| H | 5-SOCH₃ | H | CH₃ | CH₃ | OCH₃ | OCH₃ | CH | |
| H | 5-SO₂CH₂CH₃ | H | CH₃ | CH₃ | OCH₃ | OCH₃ | CH | |
| H | 5-SO₂N(CH₃)₂ | H | CH₃ | CH₃ | OCH₃ | OCH₃ | CH | |
| H | 5-CN | H | CH₃ | CH₃ | OCH₃ | OCH₃ | CH | |
| H | 5-CO₂CH₂CH₃ | H | CH₃ | CH₃ | OCH₃ | OCH₃ | CH | |
| H | 5-CO₂CH₂CH₂I | H | CH₃ | CH₃ | OCH₃ | OCH₃ | CH | |
| H | 5-CO₂CH₂CH₂CN | H | CH₃ | CH₃ | OCH₃ | OCH₃ | CH | |
| H | 5-COcyclohexyl | H | CH₃ | CH₃ | OCH₃ | OCH₃ | CH | |
| H | 5-OCH₂CF₃ | H | CH₃ | CH₃ | OCH₃ | OCH₃ | CH | |
| H | 5-SCF₂CF₃ | H | CH₃ | CH₃ | OCH₃ | OCH₃ | CH | |
| H | 6-Cl | H | CH₃ | CH₃ | OCH₃ | OCH₃ | CH | |
| H | 6-Br | H | CH₃ | CH₃ | OCH₃ | OCH₃ | CH | |
| H | 6-CH₃ | H | CH₃ | CH₃ | OCH₃ | OCH₃ | CH | |
| H | 6-CH₃O | H | CH₃ | CH₃ | OCH₃ | OCH₃ | CH | |
| H | 6-SO₂CH₃ | H | CH₃ | CH₃ | OCH₃ | OCH₃ | CH | |
| H | 6-SO₂CH₂CH₂CH₃ | H | CH₃ | CH₃ | OCH₃ | OCH₃ | CH | |
| H | 6-CO₂CH₃ | H | CH₃ | CH₃ | OCH₃ | OCH₃ | CH | |
| H | 6-SO₂N(CH₃)OCH₃ | H | CH₃ | CH₃ | OCH₃ | OCH₃ | CH | |
| H | 6-SO₂N(CH₃)₂ | H | CH₃ | CH₃ | OCH₃ | OCH₃ | CH | |
| H | 6-SO₂N-pyrrolidino | H | CH₃ | CH₃ | OCH₃ | CH₃ | CH | |
| H | 6-SO₂N-morpholino | H | CH₃ | CH₃ | OCH₃ | OCH₃ | CH | |
| H | 6-SO₂N-morpholino | H | CH₃ | CH₃ | Cl | CH₃ | CH | |
| CH₃ | H | H | CH₃ | CH₃ | CH₃ | CH₃ | CH | |
| CH₃ | H | H | CH₃ | CH₃ | CH₃ | OCH₃ | CH | |
| CH₃ | H | H | CH₃ | CH₃ | OCH₃ | CH₃ | CH | |
| CH₃ | H | H | CH₃ | CH₃ | OCH₃ | OCH₃ | CH | |
| CH₃ | H | H | CH₃ | —CH₂CH₂OCH₂CH₂— | OCH₃ | CH₃ | N | |
| CH₃ | H | H | CH₃ | —CH₂CH₂CH₂CH₂— | OCH₃ | CH₃ | N | |
| CH₃ | H | H | CH₃ | CH₂CH=CH₂ | OCH₃ | CH₃ | N | |
| CH₃ | H | COCH₃ | C₆H₅ | C₆H₅ | OCH₃ | CH₃ | N | |
| CH₃ | H | COCH₃ | 2-Cl—C₆H₄ | H | OCH₃ | CH₃ | N | |
| CH₃ | H | CH₃ | C₆H₅ | H | OCH₃ | CH₃ | N | |
| CH₃ | H | H | CH₂CF₃ | H | OCH₃ | CH₃ | N | |
| CH₃ | H | CONHCH₃ | CH₃ | H | OCH₃ | OCH₃ | N | |
| CH₃ | H | H | C₂H₅ | H | OCH₃ | CH₃ | CH | |
| CH₃ | 6-Cl | CH₃ | C₆H₅ | H | OCH₃ | CH₃ | CH | |
| CH₃ | H | CH₃ | 2-Cl—C₆H₄ | CH₃ | OCH₃ | CH₃ | CH | |
| H | H | H | CH₃ | H | OCH₃ | OCH₃ | CH | |
| H | 5-CH₂OCH₃ | H | CH₃ | CH₃ | OCH₃ | OCH₃ | CH | |
| H | 5-CH₂OCH₂CH₂Cl | H | CH₃ | CH₃ | OCH₃ | OCH₃ | CH | |
| H | 5-CH₂OCH₂CF₃ | H | CH₃ | CH₃ | OCH₃ | CH₃ | CH | |
| H | 5-CH₂SCH₃ | H | CH₃ | CH₃ | OCH₃ | OCH₃ | CH | |
| H | 5-CH₂SCH₂CH₂F | H | CH₃ | CH₃ | OCH₃ | OCH₃ | CH | |

TABLE I-continued

Formula I, A = A-1, W = O

| R | R₁ | R₂ | R₃ | R₄ | X | Y | Z | m.p. (°C.) |
|---|---|---|---|---|---|---|---|---|
| H | 5-CH₂CN | H | CH₃ | CH₃ | OCH₃ | CH₃ | CH | |
| H | 5-CH₂CH₂CN | H | CH₃ | CH₃ | OCH₃ | OCH₃ | N | |
| CH₃ | H | C₆H₅ | C₆H₅ | H | OCH₃ | CH₃ | CH | |
| CH₃ | H | CH₃ | H | H | OCH₃ | CH₃ | CH | |
| CH₃ | H | C₂H₅ | H | H | OCH₃ | CH₃ | CH | |
| H | H | H | C₆H₅ | H | OCH₃ | OCH₃ | N | |
| H | H | H | C₆H₅ | H | CH₃ | CH₃ | CH | |
| H | H | CH₃ | CH₃ | CH₃ | CH₃ | CH₃ | CH | |
| H | H | CH₃ | CH₃ | CH₃ | OCH₃ | OCH₃ | CH | |
| H | H | CH₃ | CH₃ | CH₃ | Cl | OCH₃ | CH | |
| H | 5-NH₂ | H | C₆H₅ | H | OCH₃ | OCH₃ | N | |
| H | 5-N(CH₃)₂ | H | H | H | OCH₃ | CH₃ | CH | |
| H | 5-N(CH₃)CH₂CH₃ | H | CH₃ | CH₃ | OCH₃ | OCH₃ | CH | |

TABLE Ia

Formula I, A = A-1, W = S

| R | $R_1$ | $R_2$ | $R_3$ | $R_4$ | X | Y | Z | m.p.(°C.) |
|---|---|---|---|---|---|---|---|---|
| H | H | H | $CH_3$ | $CH_3$ | $CH_3$ | $OCH_3$ | CH | |
| H | H | H | $CH_3$ | $CH_3$ | $OCH_3$ | $OCH_3$ | CH | |
| H | H | H | $CH_3$ | $CH_3$ | $CH_3$ | $OCH_3$ | N | |
| H | H | $CH_3$ | $CH_3$ | $CH_3$ | $CH_3$ | $OCH_3$ | CH | |
| H | H | $CH_3$ | $CH_3$ | $CH_3$ | $OCH_3$ | $OCH_3$ | CH | |
| H | H | $CH_3$ | $CH_3$ | $CH_3$ | Cl | $OCH_3$ | CH | |

TABLE Ia-continued

Formula I, A = A-1, W = S

| R | $R_1$ | $R_2$ | $R_3$ | $R_4$ | X | Y | Z | m.p.(°C.) |
|---|---|---|---|---|---|---|---|---|
| H | H | $CH_3$ | $CH_3$ | $CH_3$ | $CH_3$ | $OCH_3$ | N | |
| H | H | H | $C_6H_5$ | H | $OCH_3$ | $OCH_3$ | CH | |
| H | H | H | $COC_6H_5$ | H | $OCH_3$ | $OCH_3$ | CH | |
| H | H | H | H | H | $OCH_3$ | $OCH_3$ | CH | |
| H | H | H | $CH_3$ | H | $OCH_3$ | $OCH_3$ | CH | |

TABLE II

Formula I, W = O

| R | $R_1$ | $R_2$ | $R_3$ | $R_4$ | A | $X_1$ | $X_2$ | $X_3$ | $Y_1$ | $Y_2$ | $Y_3$ | m.p. (°C.) |
|---|---|---|---|---|---|---|---|---|---|---|---|---|
| H | H | H | H | H | A-2 | $CH_3$ | — | — | O | — | — | |
| H | H | H | H | $CH_3$ | A-2 | $CH_3$ | — | — | O | — | — | |
| H | H | H | H | $C_2H_5$ | A-2 | $OCH_3$ | — | — | O | — | — | |
| H | H | H | H | $C_6H_5$ | A-2 | $CH_3$ | — | — | O | — | — | |
| H | H | H | $n$-$C_7H_9$ | H | A-2 | $OCH_3$ | — | — | $CH_2$ | — | — | |
| H | H | H | $CH_2C\equiv CH$ | H | A-2 | $OCH_3$ | — | — | $CH_2$ | — | — | |
| H | H | H | 4-Cl—$C_6H_4$ | H | A-2 | $OCH_3$ | — | — | $CH_2$ | — | — | |
| H | H | H | 2-$CH_3O$—$C_6H_4$ | H | A-2 | $OCH_3$ | — | — | $CH_2$ | — | — | |
| H | H | $CH_3$ | H | H | A-2 | $CH_3$ | — | — | $CH_2$ | — | — | |
| H | H | $COC_2H_5$ | H | H | A-2 | $OCH_2CH_3$ | — | — | O | — | — | |
| H | H | $COC_6H_4$—2-Cl | H | H | A-2 | $OCH_3$ | — | — | O | — | — | |
| H | H | $CH_3$ | $CH_3$ | H | A-2 | $OCH_3$ | — | — | O | — | — | |
| H | H | $CH_3$ | $CH_3$ | H | A-2 | $OCF_2H$ | — | — | O | — | — | |
| H | H | $CH_3$ | $CH_3$ | H | A-2 | $CH_3$ | — | — | O | — | — | |
| H | H | $CH_3$ | $CH_3$ | H | A-2 | $CH_3$ | — | — | $CH_2$ | — | — | |
| H | H | $CH_3$ | $CH_3$ | H | A-2 | $OCF_2H$ | — | — | $CH_2$ | — | — | |
| H | H | $CH_3$ | $CH_3$ | H | A-2 | $OCH_3$ | — | — | $CH_2$ | — | — | |
| H | H | $CH_3$ | $CH_3$ | H | A-2 | $OCH_2CH_3$ | — | — | $CH_2$ | — | — | |
| H | H | $CH_3$ | $C_6H_5$ | H | A-2 | $OCH_3$ | — | — | O | — | — | |
| H | H | $CH_3$ | $C_6H_5$ | H | A-2 | $CH_3$ | — | — | O | — | — | |
| H | H | $CH_3$ | $C_6H_5$ | H | A-2 | $CH_3$ | — | — | $CH_2$ | — | — | |
| H | H | $CH_3$ | $C_6H_5$ | $C_6H_5$ | A-2 | $CH_3$ | — | — | $CH_2$ | — | — | |
| H | H | $CH_3$ | $C_6H_5$ | $C_6H_5$ | A-2 | $OCH_3$ | — | — | $CH_2$ | — | — | |
| H | H | $CH_3$ | $C_6H_5$ | $C_6H_5$ | A-2 | $OCF_2H$ | — | — | $CH_2$ | — | — | |
| H | H | $CH_3$ | $C_6H_5$ | $C_6H_5$ | A-2 | $OCH_3$ | — | — | O | — | — | |
| H | H | $CH_3$ | $C_6H_5$ | $CH_3$ | A-2 | $OCH_3$ | — | — | O | — | — | |
| H | H | $CH_3$ | $C_6H_5$ | $CH_3$ | A-2 | $OCH_3$ | — | — | $CH_2$ | — | — | |
| H | H | $CH_3$ | $CH_3$ | $CH_3$ | A-2 | $CH_3$ | — | — | $CH_2$ | — | — | |
| H | H | $CH_3$ | $CH_3$ | $CH_3$ | A-2 | $OCH_3$ | — | — | $CH_2$ | — | — | |
| H | H | $CH_3$ | $CH_3$ | $CH_3$ | A-2 | $OC_2H_5$ | — | — | $CH_2$ | — | — | |
| H | H | $CH_3$ | $CH_3$ | $CH_3$ | A-2 | $OCF_2H$ | — | — | $CH_2$ | — | — | |
| H | H | $CH_3$ | $CH_3$ | $CH_3$ | A-2 | $OCH_3$ | — | — | O | — | — | |
| H | H | $CH_3$ | $CH_3$ | $CH_3$ | A-2 | $CH_3$ | — | — | O | — | — | |
| H | 5-$CH_3O$ | $CH_3$ | $CH_3$ | $CH_3$ | A-2 | $CH_3$ | — | — | O | — | — | |
| H | 6-Cl | $CH_3$ | $CH_3$ | $CH_3$ | A-2 | $CH_3$ | — | — | $CH_2$ | — | — | |
| $CH_3$ | H | $CH_3$ | $CH_3$ | $CH_3$ | A-2 | $OCH_3$ | — | — | $CH_2$ | — | — | |
| $CH_3$ | H | $CH_3$ | $CH_3$ | $CH_3$ | A-2 | $OCH_3$ | — | — | O | — | — | |
| H | H | H | H | H | A-3 | $CH_3$ | — | — | — | — | — | |
| H | H | H | H | H | A-3 | $OCH_3$ | — | — | — | — | — | |
| H | H | H | H | $CH_3$ | A-3 | $CH_3$ | — | — | — | — | — | |
| H | H | H | H | $CH_3$ | A-3 | $OCH_3$ | — | — | — | — | — | |
| H | H | H | $CH_3$ | $CH_3$ | A-3 | $OCH_3$ | — | — | — | — | — | |
| H | H | H | $CH_3$ | $CH_3$ | A-3 | $CH_3$ | — | — | — | — | — | |
| H | H | H | $CH_3$ | $CH_3$ | A-3 | $OC_2H_5$ | — | — | — | — | — | |
| H | H | H | $CH_3$ | $CH_3$ | A-3 | $OCF_2H$ | — | — | — | — | — | |
| H | H | H | $CH_3$ | $C_2H_5$ | A-3 | $CH_3$ | — | — | — | — | — | |
| H | H | H | $CH_3$ | $C_6H_5$ | A-3 | $OCH_3$ | — | — | — | — | — | |
| H | H | H | H | 4-$CF_3$—$C_6H_4$ | A-3 | $CH_3$ | — | — | — | — | — | |
| H | H | H | $CH_3$ | $C_5H_5$ | A-3 | $OCH_3$ | — | — | — | — | — | |
| H | H | H | $C_6H_5$ | $C_6H_5$ | A-3 | $CH_3$ | — | — | — | — | — | |
| H | H | H | $C_6H_5$ | $C_6H_5$ | A-3 | $OCH_3$ | — | — | — | — | — | |
| H | H | H | $C_6H_5$ | $C_6H_5$ | A-3 | $OCF_2H$ | — | — | — | — | — | |
| H | H | H | $C_6H_5$ | $C_6H_5$ | A-3 | $OC_2H_7$ | — | — | — | — | — | |
| H | H | $CH_3$ | $C_6H_5$ | $C_6H_5$ | A-3 | $OCH_3$ | — | — | — | — | — | |
| H | H | $CH_3$ | $CH_3$ | H | A-3 | $CH_3$ | — | — | — | — | — | |
| H | H | $CH_3$ | $CH_3$ | H | A-3 | $OCH_3$ | — | — | — | — | — | |
| H | H | $CO_2CH_3$ | $CH_3$ | H | A-3 | $CH_3$ | — | — | — | — | — | |
| H | H | $CO_2C_6H_5$ | $CH_3$ | H | A-3 | $OCH_3$ | — | — | — | — | — | |
| H | 4-Cl | H | $CH_3$ | H | A-3 | $OCH_3$ | — | — | — | — | — | |
| H | 5-Cl | H | $CH_3$ | H | A-3 | $OCH_3$ | — | — | — | — | — | |
| H | 5-$OCH_3$ | H | $CH_3$ | H | A-3 | $CH_3$ | — | — | — | — | — | |
| H | 6-Cl | H | $CH_3$ | H | A-3 | $CH_3$ | — | — | — | — | — | |
| $CH_3$ | H | H | $CH_3$ | H | A-3 | $OCH_3$ | — | — | — | — | — | |
| $CH_3$ | H | $CH_3$ | $CH_3$ | H | A-3 | $OCH_3$ | — | — | — | — | — | |
| H | H | H | H | H | A-4 | $CH_3$ | — | — | — | $CH_3$ | — | |
| H | H | H | H | $CH_3$ | A-4 | $OCH_3$ | — | — | — | $CH_3$ | — | |
| H | H | H | H | $C_6H_5$ | A-4 | $CH_3$ | — | — | — | H | — | |

TABLE II-continued

Formula I, W = O

| R | $R_1$ | $R_2$ | $R_3$ | $R_4$ | A | $X_1$ | $X_2$ | $X_3$ | $Y_1$ | $Y_2$ | $Y_3$ | m.p. (°C.) |
|---|---|---|---|---|---|---|---|---|---|---|---|---|
| H | H | $CH_3$ | H | H | A-4 | $CH_3$ | — | — | — | H | — | |
| H | H | H | $CH_3$ | $CH_3$ | A-4 | $OCH_3$ | — | — | — | $CH_3$ | — | |
| H | H | H | $CH_3$ | $CH_3$ | A-4 | $OCH_3$ | — | — | — | $CH_3$ | — | |
| H | H | H | $CH_3$ | $CH_3$ | A-4 | $CH_3$ | — | — | — | $CH_3$ | — | |
| H | H | H | $CH_3$ | $CH_3$ | A-4 | $OCF_2H$ | — | — | — | H | — | |
| H | H | H | $CH_3$ | $CH_3$ | A-4 | $OC_2H_5$ | — | — | — | H | — | |
| H | H | H | $CH_3$ | $C_6H_5$ | A-4 | $OCH_3$ | — | — | — | H | — | |
| H | H | H | $C_6H_5$ | $C_6H_5$ | A-4 | $OCH_3$ | — | — | — | $CH_3$ | — | |
| H | H | $CH_3$ | $CH_3$ | H | A-4 | $OCH_3$ | — | — | — | H | — | |
| H | H | $CH_3$ | $CH_3$ | H | A-4 | $CH_3$ | — | — | — | H | — | |
| H | H | $CH_3$ | $CH_3$ | H | A-4 | $OCH_3$ | — | — | — | $CH_3$ | — | |
| H | H | $CH_3$ | $CH_3$ | H | A-4 | $OCH_2F$ | — | — | — | $CH_3$ | — | |
| H | H | $CH_3$ | $C_6H_5$ | H | A-4 | $OCH_3$ | — | — | — | H | — | |
| H | H | $CON(CH_3)_2$ | $CH_3$ | $CH_3$ | A-4 | $CH_3$ | — | — | — | H | — | |
| H | 3-$NO_2$ | H | $CH_3$ | $CH_3$ | A-4 | $OCH_3$ | — | — | — | H | — | |
| H | 4-Br | H | $CH_3$ | $C_6H_5$ | A-4 | $CH_3$ | — | — | — | $CH_3$ | — | |
| $CH_3$ | H | $CH_3$ | $CH_3$ | H | A-4 | $OCH_3$ | — | — | — | $CH_3$ | — | |
| $CH_3$ | H | $CH_3$ | $CH_3$ | H | A-4 | $CH_3$ | — | — | — | $CH_3$ | — | |
| $CH_3$ | H | H | $CH_3$ | $CH_3$ | A-4 | $CH_3$ | — | — | — | H | — | |
| $CH_3$ | H | H | $CH_3$ | $CH_3$ | A-4 | $OCH_3$ | — | — | — | H | — | |
| $CH_3$ | H | H | $C_6H_5$ | $C_6H_5$ | A-4 | $OCH_3$ | — | — | — | H | — | |
| H | H | H | $CH_3$ | $CH_3$ | A-5 | — | $OCH_3$ | — | — | — | $CH_3$ | |
| H | H | H | $CH_3$ | $CH_3$ | A-5 | — | $CH_3$ | — | — | — | $CH_3$ | |
| H | H | H | $CH_3$ | $CH_3$ | A-5 | — | $SCH_3$ | — | — | — | $C_2H_5$ | |
| H | H | H | $CH_3$ | $CH_3$ | A-5 | — | $CH_3$ | — | — | — | $CH_2CF_3$ | |
| H | H | H | $CH_3$ | $C_6H_5$ | A-5 | — | $OCH_3$ | — | — | — | $CH_3$ | |
| H | H | $CH_3$ | H | $C_6H_5$ | A-5 | — | $OCH_3$ | — | — | — | $C_2H_5$ | |
| H | H | $CH_3$ | H | $C_6H_5$ | A-5 | — | $CH_3$ | — | — | — | $CH_3$ | |
| H | H | $CH_3$ | $CH_3$ | $C_6H_5$ | A-5 | — | $OCH_3$ | — | — | — | $CH_3$ | |
| H | H | $CH_3$ | $CH_3$ | $C_6H_5$ | A-5 | — | $CH_3$ | — | — | — | $CH_3$ | |
| $CH_3$ | H | $CH_3$ | $CH_3$ | $C_6H_5$ | A-5 | — | $OCH_3$ | — | — | — | $CH_3$ | |
| $CH_3$ | H | H | $CH_3$ | $CH_3$ | A-5 | — | $CH_3$ | — | — | — | $CH_3$ | |
| $CH_3$ | 6-Cl | H | $CH_3$ | $CH_3$ | A-5 | — | $OCH_3$ | — | — | — | $CH_3$ | |
| H | H | H | $CH_3$ | $CH_3$ | A-6 | — | — | $CH_3$ | — | — | — | |
| H | H | H | $CH_3$ | $CH_3$ | A-6 | — | — | $OCH_3$ | — | — | — | |
| H | H | H | H | $CH_3$ | A-6 | — | — | $OCH_3$ | — | — | — | |
| H | H | H | H | $C_6H_5$ | A-6 | — | — | $CH_3$ | — | — | — | |
| H | H | $COCH_3$ | H | $C_6H_5$ | A-6 | — | — | $CH_3$ | — | — | — | |
| H | H | $CH_3$ | $CH_3$ | H | A-6 | — | — | $CH_3$ | — | — | — | |
| H | H | $CH_3$ | $CH_3$ | H | A-6 | — | — | $OCH_3$ | — | — | — | |
| H | H | $CH_3$ | $C_6H_5$ | H | A-6 | — | — | $OCH_3$ | — | — | — | |
| H | H | $CH_3$ | 2-Cl—$C_6H_4$ | H | A-6 | — | — | $OCH_3$ | — | — | — | |
| H | 5-$CH_3O$ | H | $CH_3$ | $CH_3$ | A-6 | — | — | $CH_3$ | — | — | — | |
| $CH_3$ | 5-$CH_3O$ | H | $CH_3$ | $CH_3$ | A-6 | — | — | $CH_3$ | — | — | — | |
| $CH_3$ | 5-$CH_3O$ | $CH_3$ | $CH_3$ | H | A-6 | — | — | $CH_3$ | — | — | — | |

TABLE IIa

Formula I, W = S

| R | $R_1$ | $R_2$ | $R_3$ | $R_4$ | A | $X_1$ | $X_2$ | $X_3$ | $Y_1$ | $Y_2$ | $Y_3$ | m.p. (°C.) |
|---|---|---|---|---|---|---|---|---|---|---|---|---|
| H | H | H | $CH_3$ | $CH_3$ | A-2 | $OCH_3$ | — | — | O | — | — | |
| H | H | $CH_3$ | $CH_3$ | $CH_3$ | A-2 | $OCH_3$ | — | — | $CH_2$ | — | — | |
| H | H | H | $CH_3$ | $CH_3$ | A-3 | $CH_3$ | — | — | — | — | — | |
| H | H | $CH_3$ | $CH_3$ | $CH_3$ | A-3 | $OCH_3$ | — | — | — | — | — | |
| H | H | H | $CH_3$ | $CH_3$ | A-4 | $CH_3$ | — | — | — | $CH_3$ | — | |
| H | H | $CH_3$ | $CH_3$ | $CH_3$ | A-4 | $OCH_3$ | — | — | — | $CH_3$ | — | |
| H | H | H | $CH_3$ | $CH_3$ | A-5 | — | $OCH_3$ | — | — | — | $CH_3$ | |
| H | H | $CH_3$ | $CH_3$ | $CH_3$ | A-5 | — | $OCH_3$ | — | — | — | $CH_2CF_3$ | |
| H | H | H | $CH_3$ | $CH_3$ | A-6 | — | — | $OCH_3$ | — | — | — | |
| H | H | $CH_3$ | $CH_3$ | $CH_3$ | A-6 | — | — | $OCH_3$ | — | — | — | |

Formulations

Useful formulations of the compounds of the Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE III

|  | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable | 3-50 | 40-95 | 0-15 |

TABLE III-continued

| | Active Ingredient | Weight Percent* Diluent(s) | Surfactant(s) |
|---|---|---|---|
| Concentrates) | | | |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

In the following examples, all parts are by weight unless otherwise indicated.

EXAMPLE 3

Wettable Powder 2-(2,2-Dimethylhydrazinosulfonyl)N-[(4-methoxy-6-methyl-1,3,5-triazin-2-yl)aminocarbonyl]benzenesulfonamide: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 4

Wettable Powder 2-(2,2-Dimethylhydrazinosulfonyl)-N-[(4,6-dimethoxypyrimidin-2-yl)aminocarbonyl]benzenesulfonamide: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 5

Granule

Wettable Powder of Example 4: 5%
attapulgite granules (U.S.S. 20–40 mesh; 0.84–0.42 mm): 95%

A slurry of wettable powder containing 25% solids is sprayed on the surface of attapulgite granules in a double-cone blender. The granules are dried and packaged.

EXAMPLE 6

Extruded Pellet 2-(2,2-Dimethylhydrazinosulfonyl)-N-[(4,6-dimethoxypyrimidin-2-yl)aminocarbonyl]benzenesulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

Low Strength Granule 2-(2,2-Dimethylhydrazinosulfonyl)N-[(4-methoxy-6-methyl-1,3,5-triazin-2-yl)aminocarbonyl]benzenesulfonamide: 0.1%
attapulgite granules (U.S.S. 20–40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 8

Granule 2-(2,2-Dimethylhydrazinosulfonyl)N-[(4-methoxy-6-methyl-1,3,5-triazin-2-yl)aminocarbonyl]benzenesulfonamide: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less then 1%. The material is then discharged, screened to the desired size range, generally 14-100 mesh (1410-149 microns), and packaged for use.

EXAMPLE 9

Low Strength Granule 2-(2,2-Dimethylhydrazinosulfonyl)-N-[(4,6-dimethoxypyrimidin-2-yl)aminocarbonyl]benzenesulfonamide: 1%
N,N-dimethylformamide: 9%
attapulgite granules (U.S.S. 20-40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension 2-(2,2-Dimethylhydrazinosulfonyl)-N-[(4,6-dimethoxypyrimidin-2-yl)aminocarbonyl]benzenesulfonamide: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 11

Solution 2-(2,2-Dimethylhydrazinosulfonyl)N-[(4-methoxy-6-methyl-1,3,5-triazin-2-yl)aminocarbonyl]benzenesulfonamide, sodium salt: 5%
water: 95%

The salt is added directly to the water with stirring to produce the solution, which may then be packaged for use.

EXAMPLE 12

High Strength Concentrate 2-(2,2-Dimethylhydrazinosulfonyl)-N-[(4,6-dimethoxypyrimidin-2-yl)aminocarbonyl]benzenesulfonamide: 99%
silica aerogel: 0.5%
synthetic amorphous silica: 0.5%

The ingredients are blended and ground in a hammermill to produce a material essentially all passing a U.S.S. No. 50 screen (0.3 mm opening). The concentrate may be formulated further if necessary.

EXAMPLE 13

Wettable Powder 2-(2,2-Dimethylhydrazinosulfonyl)N-[(4-methoxy-6-methyl-1,3,5-triazin-2-yl)aminocarbonyl]benzenesulfonamide: 90%
dioctyl sodium sulfosuccinate: 0.1%
synthetic fine silica: 9.9%

The ingredients are blended and ground in a hammermill to produce particles essentially all below 100 microns. The material is sifted through a U.S.S. No. 50 screen and then packaged.

EXAMPLE 14

Wettable Powder 2-(2,2-Dimethylhydrazinosulfonyl)-N-[(4,6-dimethoxypyrimidin-2-yl)aminocarbonyl]benzenesulfonamide: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 15

Oil Suspension 2-(2,2-Dimethylhydrazinosulfonyl)N-[(4-methoxy-6-methyl-1,3,5-triazin-2yl)aminocarbonyl]benzenesulfonamide: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

EXAMPLE 16

Dust 2-(2,2-Dimethylhydrazinosulfonyl)-N-[(4,6-dimethoxypyrimidin-2-yl)aminocarbonyl]benzenesulfonamide: 10%
attapulgite: 10%
Pyrophyllite: 80%

The active ingredient is blended with attapulgite and then passed through a hammer-mill to produce particles substantially all below 200 microns. The ground concentrate is then blended with powdered pyrophyllite until homogeneous.

EXAMPLE 17

Oil Suspension 2-(2,2-Dimethylhydrazinosulfonyl)N-[(4-methoxy-6-methyl-1,3,5-triazin-2-yl)aminocarbonyl]benzenesulfonamide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 18

Wettable Powder 2-(2,2-Dimethylhydrazinosulfonyl)-N-[(4,6-dimethoxypyrimidin-2yl)aminocarbonyl]benzenesulfonamide: 20%
sodium alkylnaphthalenesulfonate: 4%
sodium ligninsulfonate: 4%
low viscosity methyl cellulose: 3% attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

Utility

Test results indicate that the compounds of the present invention are highly active preemergent or post emergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyard-grass (Echinochloa crusgalli), wild oats (Avena fatua), cheatgrass (Bromus secalinus) velvetleaf (Abutilon theophrasti), morningglory (Ipomoea spp.), cocklebur (Xanthium pennsylvanicum), sorghum, corn, soybean, sugarbeet, cotton, rice, wheat and purple nutsedge (Cyperus rotundus) tubers were planted and treated preemergence with the test chemicals dissolved in a nonphytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

Compounds

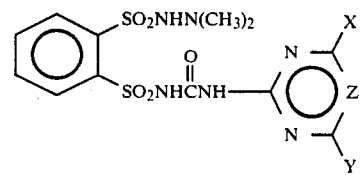

| Compound | X | Y | Z |
|---|---|---|---|
| 1 | CH3 | CH3 | CH |
| 2 | OCH3 | CH3 | CH |
| 3 | OCH3 | OCH3 | CH |
| 4 | Cl | OCH3 | CH |
| 5 | CH3 | OCH3 | N |
| 6 | OCH3 | OCH3 | N |

TABLE A

| Rate (kg/ha) | Cmpd. 1 0.05 | Cmpd. 2 0.05 | Cmpd. 3 0.05 | Cmpd. 4 0.05 | Cmpd. 4 0.10 | Cmpd. 5 0.05 | Cmpd. 5 0.10 | Cmpd. 6 0.05 | Cmpd. 6 0.40 |
|---|---|---|---|---|---|---|---|---|---|
| POSTEMERGENCE | | | | | | | | | |
| Morningglory | 1C,5G | 2C,3H | 9C | 2C,5G | 4C,9G | 3C,8H | 9C | 3C,8H | 4C,9G |
| Cocklebur | 1H | 7G | 7G | 5G | 6G | 8G | 2C,8G | 2G | 5G |
| Velvetleaf | 7G | 5C,8G | 9C | 2G | 4G | 5C,9G | 10C | 1C,3G | 5C,8G |
| Nutsedge | 5G | 0 | 2C,9G | 5G | 5G | 0 | 5G | 0 | 0 |
| Crabgrass | 0 | 3G | 4G | 0 | 0 | 0 | 5G | 0 | 2G |
| Barnyardgrass | 9H | 3C,9H | 3C,8H | 3H | 4H | 2H | 8H | 0 | 2H |
| Cheatgrass | 5G | 6G | 4C,9G | 0 | 4G | 0 | 4G | 0 | 0 |
| Wild Oats | 0 | 3G | 6G | 0 | 0 | 0 | 0 | 0 | 0 |
| Wheat | 0 | 5G | 2G | 0 | 0 | 0 | 0 | 0 | 0 |
| Corn | 2C,8H | 4C,9G | 2C,8G | 2H | 3H | 2C,9G | 2U,9G | 5H | 2U,9G |
| Soybean | 2C,6G | 9C | 9C | 1H | 2H | 9C | 5C,9G | 2C,8G | 5C,9G |
| Rice | 2C,9G | 5C,9G | 6C,9G | 4G | 2C,8G | 5G | 2C,9G | 0 | 6C,9G |
| Sorghum | 3C,9H | 3C,9H | 4C,9H | 5H | 3G | 2C,6H | 3C,9H | 2G | 2C,7G |
| Sugar Beets | 5C,9G | 9C | 9C | 3H | 3C,7H | 5C,9G | 9C | 4C,8G | 9C |
| Cotton | 2C,5G | 2C,6G | 2C,6G | 2G | 5C,9G | 4C,8H | 5C,9G | 4C,6G | 4C,8G |
| PREEMERGENCE | | | | | | | | | |
| Morningglory | 4G | 7G | 7G | 7H | 7G | 5G | 7G | 0 | 7G |
| Cocklebur | 2G | 5G | — | 5G | 7G | 2G | 6G | 0 | 7H |
| Velvetleaf | 2G | 8G | 9G | 4G | 5G | 2G | 5G | 0 | 7G |
| Nutsedge | 0 | 10E | 8G | 0 | 0 | 0 | 0 | 0 | 0 |
| Crabgrass | 0 | 0 | 0 | 0 | 0 | 0 | 0 | 0 | 0 |
| Barnyardgrass | 0 | 2C,8H | 2C | 0 | 0 | 0 | 0 | 0 | 0 |

TABLE A-continued

| Rate (kg/ha) | Cmpd. 1 0.05 | Cmpd. 2 0.05 | Cmpd. 3 0.05 | Cmpd. 4 0.05 | Cmpd. 4 0.10 | Cmpd. 5 0.05 | Cmpd. 5 0.10 | Cmpd. 6 0.05 | Cmpd. 6 0.40 |
|---|---|---|---|---|---|---|---|---|---|
| Cheatgrass | 6G | 8G | 6G | 0 | 0 | 0 | 0 | 0 | 0 |
| Wild Oats | 0 | 2C,6G | 2C,6G | 0 | 0 | 0 | 0 | 0 | 0 |
| Wheat | 3G | 5G | 2C,6G | 0 | 0 | 0 | 0 | 0 | 0 |
| Corn | 2C,6G | 2C,8G | 5G | 3G | 2C,7G | 2C,5G | 8G | 0 | 2C,8G |
| Soybean | 0 | 7G | 2C,5G | 0 | 2G | 2C,5G | 6G | 0 | 5G |
| Rice | 5G | 8H | 3C,7H | 3G | 6G | 0 | 5G | 0 | 6G |
| Sorghum | 2C,3G | 2C,8H | 5G | 2G | 3G | 4G | 2C,7G | 0 | 3C,7G |
| Sugar Beets | 7G | 9G | 8G | 4G | 8G | 3C,7G | 4C,9G | 6G | 4C,8G |
| Cotton | 5G | 8G | 7G | 3G | 7G | 8G | 7G | 4G | 2C,7G |

The embodiments of the invention in which an exclusive property or privilege is claimed are defined as follows:

1. A compound of the formula

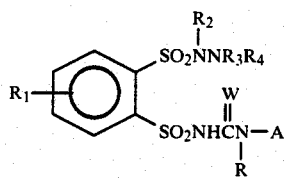

and their agriculturally suitable salts, wherein:
W is O or S;
R is H or $CH_3$;
$R_1$ is H, $C_1$ to $C_3$ alkyl, $C_1$ to $C_3$ haloalkyl, halogen, nitro, $C_1$ to $C_3$ alkoxy, $SO_2NR_aR_b$, $C_1$ to $C_3$ alkylthio, $C_1$ to $C_3$ alkylsulfinyl, $C_1$ to $C_3$ alkylsulfonyl, CN, $CO_2R_c$, $C_1$ to $C_3$ haloalkoxy, $C_1$ to $C_3$ haloalkylthio, $C_2$ to $C_3$ alkoxyalkyl, $C_2$ to $C_3$ haloalkoxyalkyl, $C_2$ to $C_3$ alkylthioalkyl, $C_2$ to $C_3$ haloalkylthioalkyl, $C_2$ to $C_3$ cyanoalkyl, or $NR_dR_e$;
$R_a$ is H, $C_1$ to $C_4$ alkyl, $C_2$ to $C_3$ cyanoalkyl, methoxy or ethoxy;
$R_b$ is H, $C_1$ to $C_4$ alkyl or $C_3$ to $C_4$ alkenyl; or
$R_a$ and $R_b$ can be taken together as $-(CH_2)_3-$, $-(CH_2)_4-$, $-(CH_2)_5-$ or $-CH_2CH_2OCH_2CH_2-$;
$R_c$ is $C_1$ to $C_4$ alkyl, $C_3$ to $C_4$ alkenyl, $C_3$ to $C_4$ alkynyl, $C_2$ to $C_4$ haloalkyl, $C_2$ to $C_3$ cyanoalkyl, $C_5$ to $C_6$ cycloalkyl, $C_4$ to $C_7$ cycloalkylalkyl or $C_2$ to $C_4$ alkoxyalkyl;
$R_d$ and $R_e$ are independently H or $C_1$ to $C_2$ alkyl;
$R_2$, $R_3$ and $R_4$ are independently H, $C_1$ to $C_4$ alkyl, $C_3$ to $C_4$ alkenyl, $C_3$ to $C_4$ alkynyl, $C_1$ to $C_4$ haloalkyl, $C(O)R_5$, $CO_2R_6$, $C(O)NR_7R_8$, $C(S)NR_7R_8$, $C(NR)NR_7R_8$, Q, CHRQ, $CH_2CH_2Q$, $C_2$ to $C_3$ alkyl substituted with $OR_9$, phenyl which may be optionally substituted with $R_{10}$ and $R_{11}$ or

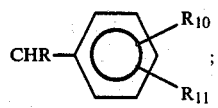

$R_3$ and $R_4$ can be taken together to form $-(CH_2)_4-$, $-(CH_2)_5-$, $CH_2CH_2OCH_2CH_2$, $CH=CHCH=CH$, $CH=N-N=CH$ or

$R_5$ is $C_1$ to $C_3$ alkyl or phenyl which can be optionally substituted with $R_{10}$ and $R_{11}$;
$R_6$ is $C_1$ to $C_3$ alkyl;
$R_7$ and $R_8$ are independently H or $C_1$ to $C_3$ alkyl;
$R_9$ is H, $SO_2R_6$, $C(O)R_6$, $CO_2R_6$, $C(O)NR_7R_8$, $C_1$ to $C_3$ alkyl, $C_1$ to $C_3$ haloalkyl or $P(O)(OR_6)_2$;
$R_{10}$ and $R_{11}$ are independently H, $C_1$ to $C_3$ alkyl, Cl, F, Br, $NO_2$, $CF_3$, CN or $C_1$ to $C_3$ alkoxy;
$R_{12}$ and $R_{13}$ are independently H, $C_1$ to $C_3$ alkyl, phenyl which can be optionally substituted with $R_{10}$ and $R_{11}$ or

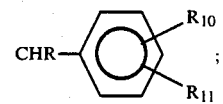

$R_{12}$ and $R_{13}$ can be taken together to form $-(CH_2)_4-$ or $-(CH_2)_5-$;
Q is a saturated 5- or 6-membered ring which is bonded through a carbon atom and contains 1 heteroatom selected from oxygen, sulfur, or nitrogen or an unsaturated or partially unsaturated 5- or 6-membered ring which is bonded through a carbon atom and contains 1 to 3 heteroatoms selected from 1 sulfur, 1 oxygen or 1 to 3 nitrogen; and Q may be optionally substituted by one or more groups selected from L;
L is $C_1$ to $C_4$ alkyl, $C_1$ to $C_3$ haloalkyl, halogen, $C_1$ to $C_3$ alkoxy, $C_1$ to $C_3$ alkylthio, $C_3$ to $C_4$ alkenyloxy, $C_3$ to $C_4$ alkenylthio, $C_1$ to $C_2$ haloalkoxy, or $C_1$ to $C_2$ haloalkylthio;
A is

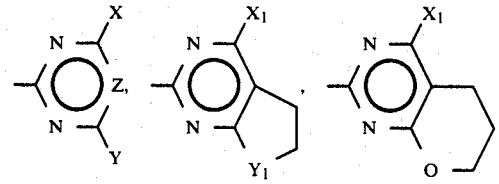

A-1    A-2    A-3

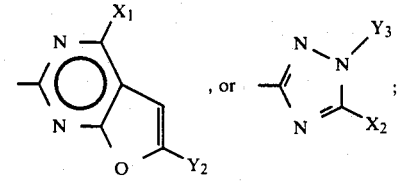

A-4    A-5

X is H, $C_1$ to $C_4$ alkyl, $C_1$ to $C_4$ alkoxy, $C_1$ to $C_4$ haloalkoxy, $C_1$ to $C_4$ haloalkyl, $C_1$ to $C_4$ haloalkylthio, $C_1$ to $C_4$ alkylthio, halogen, $C_2$ to $C_5$ alkoxyalkyl, $C_2$ to $C_5$ alkoxyalkoxy, amino, $C_1$ to $C_3$ alkylamino or di($C_1$ to $C_3$ alkyl)amino;

Y is H, $C_1$ to $C_4$ alkyl, $C_1$ to $C_4$ alkoxy, $C_1$ to $C_4$ haloalkoxy, $C_1$ to $C_4$ haloalkylthio, $C_1$ to $C_4$ alkylthio, $C_2$ to $C_5$ alkoxyalkyl, $C_2$ to $C_5$ alkoxyalkoxy, amino, $C_1$ to $C_3$ alkylamino, di($C_1$ to $C_3$ alkyl)amino, $C_3$ to $C_4$ alkenyloxy, $C_3$ to $C_4$ alkynyloxy, $C_2$ to $C_5$ alkylthioalkyl, $C_1$ to $C_4$ haloalkyl, $C_3$ to $C_5$ cycloalkyl, $C_2$ to $C_4$ alkynyl, $C(O)R_4$,

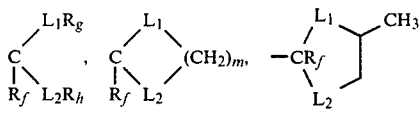

or $N(OCH_3)CH_3$;

m is 2 or 3;

$L_1$ and $L_2$ are independently O or S;

$R_f$ is H or $CH_3$;

$R_g$ and $R_h$ are independently $C_1$ to $C_2$ alkyl;

Z is CH;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$;

$Y_3$ is $CH_3$, $CH_2CH_3$ or $CH_2CF_3$;

provided that:

(a) when X is Cl, F, Br or I, Y is $OCH_3$, $OC_2H_5$, $N(OCH_3)CH_3$, $NHCH_3$ or $N(CH_3)_2$;

(b) the total number of carbon atoms in $R_2$, $R_3$ and $R_4$ does not exceed 10.

2. A compound according to claim 1 wherein:

W is O;

R is H;

$R_1$ is H, $C_1$ to $C_2$ alkyl, F, Cl, Br, $NO_2$, $C_1$ to $C_2$ alkoxy, $C_1$ to $C_2$ alkylthio, $C_1$ to $C_2$ haloalkoxy, $CH_2OCH_3$, $CH_2SCH_3$ or $CH_2CN$ and is not para to the sulfonylurea bridge;

A is A-1;

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$;

Y is H, $C_1$ to $C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $OCF_2H$, $SCF_2H$, cyclopropyl, $C\equiv CH$, $C\equiv CCH_3$ or $CH(OCH_3)_2$.

3. A compound according to claim 2 wherein: $R_2$, $R_3$ and $R_4$ are independently H, $C_1$ to $C_3$ alkyl or phenyl provided that one of $R_2$, $R_3$ and $R_4$ must be H.

4. A compound according to claim 3 wherein:

$R_1$ is H, Cl, $OCH_3$, $OCF_2H$, $CH_2OCH_3$ or $CH_2CN$;

X is $CH_3$, $OCH_3$, $OCH_2CH_3$, CL, $OCF_2H$ or $OCH_2CF_3$; and

Y is $CH_3$, $OCH_3$, $CH_2CH_3$, $CH_2OCH_3$, $NHCH_3$ or $CH(OCH_3)_2$.

5. A compound according to claim 4: 2-(2,2-dimethylhydrazinosulfonyl)-N-[(4,6-dimethoxypyrimidin-2-yl)aminocarbonyl]benzenesulfonamide.

6. A composition for the control of undesirable vegetation consisting essentially of a compound of claim 1 and at least one of (a) a surface active agent, and (b) a solid or liquid diluent.

7. A composition for the control of undesirable vegetation consisting essentially of a compound of claim 2 and at least one of (a) a surface active agent, and (b) a solid or liquid diluent.

8. A composition for the control of undesirable vegetation consisting essentially of a compound of claim 3 and at least one of (a) a surface active agent, and (b) a solid or liquid diluent.

9. A composition for the control of undesirable vegetation consisting essentially of the compound of claim 4 and at least one of (a) a surface active agent, and (b) a solid or liquid diluent.

10. A composition for the control of undesirable vegetation consisting essentially of the compound of claim 5 and at least one of (a) a surface active agent, and (b) a solid or liquid diluent.

11. A method for the control of undesirable vegetation comprising applying to the locus of such vegetation an herbicidally effective amount of a compound of claim 1.

12. A method for the control of undesirable vegetation comprising applying to the locus of such vegetation an herbicidally effective amount of a compound of claim 2.

13. A method for the control of undesirable vegetation comprising applying to the locus of such vegetation an herbicidally effective amount of a compound of claim 3.

14. A method for the control of undesirable vegetation comprising applying to the locus of such vegetation an herbicidally effective amount of the compound of claim 4.

15. A method for the control of undesirable vegetation comprising applying to the locus of such vegetation an herbicidally effective amount of the compound of claim 5.

* * * * *